United States Patent [19]

Aschwenden et al.

[11] Patent Number: 4,883,815
[45] Date of Patent: Nov. 28, 1989

[54] HYDROCINNAMIC ACID DERIVATIVES

[75] Inventors: Werner Aschwenden, Ettingen; René Imhof, Gipf-Oberfrick, both of Switzerland; Roland Jakob-Roetne, Inzlingen, Fed. Rep. of Germany; Emilio Kyburz, Reinach, Switzerland

[73] Assignee: Hoffmann-La Roche Inc., Nutley, N.J.

[21] Appl. No.: 215,003

[22] Filed: Jul. 5, 1988

[30] Foreign Application Priority Data

Jul. 21, 1987 [CH] Switzerland .......................... 2764/87

[51] Int. Cl.$^4$ ..................... A61K 31/24; C07C 103/84
[52] U.S. Cl. :................................... 514/541; 514/252; 514/255; 514/315; 514/318; 514/332; 514/352; 514/354; 514/355; 514/357; 514/533; 514/538; 514/539; 514/540; 514/542; 514/595; 514/563; 514/616; 544/360; 544/386; 546/194; 546/233; 546/234; 546/262; 546/308; 546/316; 546/323; 546/335; 560/34; 560/36; 560/37; 560/39; 560/41; 560/42; 562/439; 562/441; 562/442; 562/448; 562/449; 562/451; 564/56; 564/153; 564/155; 564/158
[58] Field of Search .................. 560/37, 41, 34, 36, 560/39, 42; 564/164, 153, 152, 56, 155, 158; 514/538, 542, 540, 616, 541, 252, 255, 315, 318, 332, 352, 354, 355, 357, 533, 539, 595, 563; 544/360, 386; 546/194, 233, 234, 262, 308, 316, 323, 335; 562/439, 441, 442, 448, 449, 451

[56] References Cited

U.S. PATENT DOCUMENTS 3,795,683  3/1974  Brossi et al. ............... 260/340.5
4,352,752 10/1982  Ojima et al. ............... 560/41
4,732,979  3/1988  Aschwanden et al. ............... 540/461

FOREIGN PATENT DOCUMENTS 0149263 7/1985 European Pat. Off. ............... 560/41

Primary Examiner—Bruce Gray
Attorney, Agent, or Firm—Jon S. Saxe; Bernard S. Leon; William G. Isgro

[57] ABSTRACT

Hydrocinnamic acid derivatives of the formula

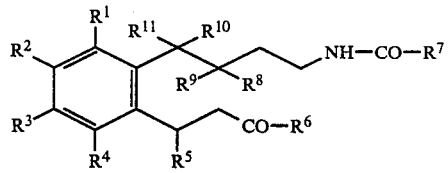

wherein
one or two of the symbols $R^1$ to $R^4$ are halogen or methoxy and the others are hydrogen;
$R^5$ is hydrogen or phenyl;
$R^6$ is a residue of the formula $-OR^{12}$ or $-NR^{13}R^{14}$;
(a)           (b)

$R^7$ is ($C_1$–$C_4$)-alkyl, ($C_2$–$C_5$)-alkanoylamino-($C_2$–$C_5$)-alkyl, amino or ($C_1$–$C_4$)-alkoxyphenyl;
$R^8$ and $R^9$ each, independently, are hydrogen or ($C_1$–$C_4$)-alkyl;
$R^{10}$ is hydrogen and $R^{11}$ is hydroxy or $R^{10}$ and $R^{11}$ taken together are oxo;
$R^{12}$ is hydrogen, ($C_1$–$C_{10}$)-alkyl, pyridylmethyl or carbamoylmethyl;
$R^{13}$ is hydrogen, ($C_1$–$C_4$)-alkyl and $R^{14}$ is hydrogen, ($C_1$–$C_4$)-alkyl, pyridyl, phenyl-($C_1$–$C_4$)-alkyl, carboxy-($C_1$–$C_4$)-alkyl, carbamoyl-($C_1$–$C_4$)-alkyl, ($C_1$–$C_4$)-alkoxy carbonyl-($C_1$–$C_4$)-alkyl, di-($C_1$–$C_4$)-alkoxy carbonyl-$C_2$–$C_5$)-alky, piperidino-$C_2$–$C_4$)-alkyl or halopyridinecarboxamido-($C_2$–$C_4$)-alkyl or $R^{13}$ and $R^{14}$ taken together with the nitrogen atom are 4-($C_1$–$C_4$)-alkyl-piperazin-1-yl, as well as pharmaceutically acceptable salts of basic compounds of formula I with acids or of acidic compounds of formula I with bases are described. The compounds of formula I and their pharmaceutically acceptable salts are suitable for the control or prevention of cerebral insufficiency or for the improvement of cognitive functions.

32 Claims, No Drawings

HYDROCINNAMIC ACID DERIVATIVES

BRIEF DESCRIPTION OF THE INVENTION

The invention relates to hydrocinnamic acid derivatives. In particular, it relates to hydrocinnamic acid derivatives of the formula

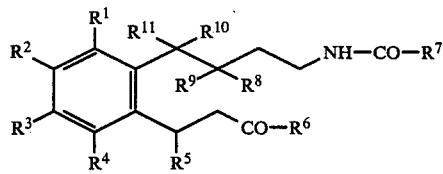

wherein
one or two of the symbols $R^1$ to $R^4$ are halogen or methoxy and the others are hydrogen;
$R^5$ is hydrogen or phenyl;
$R^6$ is a residue of the formula $$-OR^{12} \quad \text{or} \quad -NR^{13}R^{14};$$
$$\text{(a)} \qquad \qquad \text{(b)}$$

$R^7$ is $(C_1-C_4)$-alkyl, $(C_2-C_5)$-alkanoylamino-$(C_2-C_5)$-alkyl, amino or $(C_1-C_4)$-alkoxyphenyl;
$R^8$ and $R^9$ each, independently, are hydrogen or $(C_1-C_4)$-alkyl;
$R^{10}$ is hydrogen and $R^{11}$ is hydroxy or $R^{10}$ and $R^{11}$ taken together are oxo;
$R^{12}$ is hydrogen, $(C_1-C_{10})$-alkyl, pyridylmethyl or carbamoylmethyl;
$R^{13}$ is hydrogen or $(C_1-C_4)$-alkyl and $R^{14}$ is hydrogen, $(C_1-C_4)$-alkyl, pyridyl, phenyl-$(C_1-C_4)$-alkyl, carboxy-$(C_1-C_4)$-alkyl, carbamoyl-$(C_1-C_4)$-alkyl, $(C_1-C_4)$-alkoxycarbonyl-$(C_1-C_4)$-alkyl, di-$(C_1-C_4)$-alkoxycarbonyl-$(C_2-C_5)$-alkyl, piperidino-$(C_2-C_4)$-alkyl or halopyridinecarboxamido-$(C_2-C_4)$-alkyl or $R^{13}$ and $R^{14}$ together with the nitrogen atom are 4-$(C_1-C_4)$-alkyl-piperazin-1-yl,
as well as pharmaceutically acceptable salts of basic compounds of formula I with acids or of acidic compounds of formula I with bases.

DETAILED DESCRIPTION OF THE INVENTION

The invention relates to hydrocinnamic acid derivatives. In particular, it relates to hydrocinnamic acid derivatives of the formula

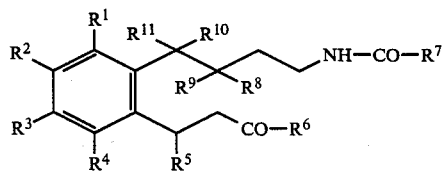

wherein
one or two of the symbols $R^1$ to $R^4$ are halogen or methoxy and the others are hydrogen;
$R^5$ is hydrogen or phenyl;
$R^6$ is a residue of the formula $$-OR^{12} \quad \text{or} \quad -NR^{13}R^{14};$$
$$\text{(a)} \qquad \qquad \text{(b)}$$

$R^7$ is $(C_1-C_4)$-alkyl, $(C_2-C_5)$-alkanoylamino-$(C_2-C_5)$-alkyl, amino or $(C_1-C_4)$-alkoxyphenyl;
$R^8$ and $R^9$ each, independently, are hydrogen or $(C_1-C_4)$-alkyl;
$R^{10}$ is hydrogen and $R^{11}$ is hydroxy or $R^{10}$ and $R^{11}$ taken together are oxo;
$R^{12}$ is hydrogen, $(C_1-C_{10})$-alkyl, pyridylmethyl or carbamoylmethyl;
$R^{13}$ is hydrogen or $(C_1-C_4)$-alkyl and $R^{14}$ is hydrogen, $(C_1-C_4)$-alkyl, pyridyl, phenyl-$(C_1-C_4)$-alkyl, carboxy-$(C_1-C_4)$-alkyl, carbamoyl-$(C_1-C_4)$-alkyl, $(C_1-C_4)$-alkoxycarbonyl-$(C_1-C_4)$-alkyl, di-$(C_1-C_4)$-alkoxycarbonyl-$(C_2-C_5)$-alkyl, piperidino-$(C_2-C_4)$-alkyl or halopyridinecarboxamido-$(C_2-C_4)$-alkyl or $R^{13}$ and $R^{14}$ together with the nitrogen atom are 4-$(C_1-C_4)$-alkyl-piperazin-1-yl,
as well as pharmaceutically acceptable salts of basic compounds of formula I with acids or of acidic compounds of formula I with bases.

The compounds of formula I and their salts are distinguished by valuable pharmacodynamic properties.

Objects of the invention are compounds of formula I and pharmaceutically acceptable salts thereof, a process for the preparation of these compounds and salts, medicaments containing these compounds and salts and the preparation of such medicaments, as well as the use of compounds of formula I and of pharmaceutically acceptable salts thereof in the control or prevention of illnesses or in the improvement of health, especially in the control or prevention of cerebral insufficiency or in the improvement of cognitive functions, and the use of compounds of formula I and of pharmaceutically acceptable salts thereof for the preparation of medicaments for the control or prevention of cerebral insufficiency or for the improvement of cognitive functions.

The term "alkyl" used in the present description denotes straight-chain or branched saturated hydrocarbon residues such as methyl, ethyl, n-propyl, isopropyl, n-butyl, isobutyl, s-butyl, t-butyl and the like. The term "alkoxy" denotes an alkyl residue in the sense of the previous definition which is attached via an oxygen atom. The term "alkanoyl" denotes residues which are derived from alkanecarboxylic acids by elimination of the hydroxyl group and accordingly embraces residues such as acetyl and the like. The term "di-alkoxycarbonylalkyl" denotes alkyl residues which are substituted by two alkoxycarbonyl groups, but not situated on the same carbon atom.

$R^4$ can preferably be hydrogen, in which case preferably either $R^1$ is chlorine and $R^2$ and $R^3$ are hydrogen or $R^1$ is hydrogen and $R^2$ and $R^3$ are chlorine or $R^1$ and $R^2$ are hydrogen and $R^3$ is fluorine, chlorine or methoxy. Preferably, $R^3$ is chlorine and $R^1$, $R^2$ and $R^4$ are hydrogen.

$R^5$ preferably is hydrogen.

When $R^6$ is a residue of formula (a) above, then $R^{12}$ preferably is hydrogen, methyl, ethyl, n-propyl, isopropyl, n-butyl, tert.-butyl, n-nonyl, 5-nonyl, 3-pyridylmethyl or carbamoylmethyl. When $R^6$ is a residue of formula (b) above, then conveniently either $R^{13}$ and $R^{14}$ both are hydrogen or both are ethyl or $R^{13}$ and $R^{14}$ together with the nitrogen atom are 4-methylpiperazin-1-yl or $R^{13}$ is hydrogen and $R^{14}$ is 4-pyridyl, 2- phenylethyl, 2-piperidinoethyl, carboxymethyl, ethoxycarbonylmethyl, carbamoylmethyl, 1-ethoxycarbonylethyl, 1,4-bis-(ethoxycarbonyl)-2-butyl or 2-(5-chloro-2-pyridinecarboxamido)ethyl. Preferably, $R^{12}$ is ethyl, n-propyl, isopropyl, n-nonyl or carbamoylmethyl or $R^{13}$ is hydrogen and $R^{14}$ is hydrogen, ethoxycarbonylmethyl or 1,4-bis-(ethoxycarbonyl)-2-butyl.

$R^7$ preferably is methyl, 3-acetylaminopropyl, amino or p-methoxyphenyl, most preferably methyl or 3-acetylaminopropyl.

Conveniently, $R^8$ and $R^9$ both are hydrogen or both are methyl, preferably both are hydrogen.

Preferably, $R^{10}$ and $R^{11}$ together are oxo.

Particularly preferred compounds of formula I are: ethyl N-[2-(4-acetamidobutyryl)-5-chlorohydrocinnamoyl]glycinate, ethyl 2-[4-(4-acetamidobutyramido)-butyryl]-5-chlorohydrocinnamate, 2-[4-(4-acetamidobutyramido)butyryl]-5-chlorohydrocinnamide, nonyl 2-(4-acetamidobutyryl)-5-chlorohydrocinnamate, ethyl 2-(4-acetamidobutyryl)-5-chlorohydrocinnamate and 2-(4-acetamidobutyryl)-N-(carbamoylmethyl)-5-chlorohydrocinnamide.

Further especially preferred compounds of formula I are: isopropyl 2-(4-acetamidobutyryl)-5-chlorohydrocinnamate, diethyl 2-[2-(4-acetamidobutyryl)-5-chlorohydrocinnamoyl]-L-glutamate and carbamoylmethyl 2-(4-acetamidobutyryl)-5-chlorohydrocinnamate.

Examples of further preferred compounds of formula I are: 2-(4-acetamidobutyryl)-5-chlorohydrocinnamide and propyl 2-(4-acetamidobutyryl)-5-chlorohydrocinnamate.

The compounds of formula I and pharmaceutically acceptable salts thereof can be prepared in accordance with the invention by (a) treating a benzazecinedione of the formula

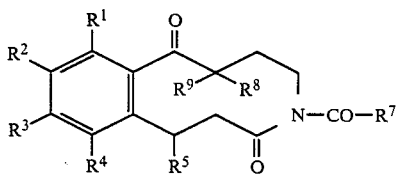

wherein $R^1$, $R^2$, $R^3$, $R^4$, $R^5$, $R^7$, $R^8$ and $R^9$ have the above significance, with an acid in the presence of a compound of the formula $HOR^{12'}$     III wherein $R^{12'}$ is hydrogen or $(C_1-C_{10})$-alkyl;

or (b) esterifying a compound of formula I in which $R^6$ is a residue of formula (a) and $R^{12}$ is hydrogen, or a reactive derivative thereof, to give a corresponding compound of formula I in which $R^6$ is a residue of formula (a) and $R^{12}$ is different from hydrogen; or (c) reacting a compound of formula I in which $R^6$ is a residue of formula (a) and $R^{12}$ is hydrogen, or a reactive derivative thereof, with a compound of the formula $HNR^{13}R^{14'}$     IV wherein $R^{13}$ has the above significance and $R^{14'}$ has the significance given above for $R^{14}$, but is not carboxy-$(C_1-C_4)$-alkyl, or reacting a compound of formula I in which $R^6$ is a residue of formula (b) and $R^{14}$ is carboxy-$(C_1-C_4)$-alkyl, or a reactive derivative thereof, with ammonia; or (d) reducing a compound of formula I in which $R^{10}$ and $R^{11}$ together are oxo; or (e) hydrolyzing a compound of formula I in which $R^6$ is a residue of formula (b) and $R^{14}$ is $(C_1-C_4)$-alkoxycarbonyl-$(C_1-C_4)$-alkyl to give a corresponding compound of formula I in which $R^6$ is a residue of formula (b) and $R^{14}$ is carboxy-$(C_1-C_4)$-alkyl; or (f) converting a basic compound of formula I into a pharmaceutically usable salt by means of an acid or converting an acidic compound of formula I into a pharmaceutically usable salt by means of a base.

Compounds of formula I in which $R^6$ is a residue of formula (a) above, $R^{12}$ is hydrogen or $(C_1-C_{10})$-alkyl and $R^{10}$ and $R^{11}$ together are oxo are obtained in accordance with process variant (a) in accordance with the invention.

If it is desired to convert a compound of formula II into a corresponding compound of formula I in which $R^6$ is a residue of formula (a) and $R^{12}$ is $(C_1-C_{10})$-alkyl, then there is used a compound of formula III in which $R^{12'}$ is $(C_1-C_{10})$-alkyl, that is, a corresponding alcohol. This alcohol can simultaneously serve as the solvent; it is, however, also possible to add a different solvent, for example, a halogenated hydrocarbon such as methylene chloride. A strong inorganic acid such as concentrated hydrochloric acid or the like is conveniently used as the acid. The reaction is conveniently effected at about room temperature and takes several (for example, 10) hours to a few (for example, 5) days.

If it is desired to convert a compound of formula II into a corresponding compound of formula I in which $R^6$ is a residue of formula (a) above and $R^{12}$ is hydrogen, then there is used a compound of formula III in which $R^{12'}$ is hydrogen, that is, water. In this case, the compound of formula II is conveniently dissolved in a polar aprotic solvent such as tetrahydrofuran, acetonitrile or the like and then aqueous acid, for example, dilute (for example, 2N) hydrochloric acid or the like, is added thereto. With respect to the reaction temperature and to the reaction duration, these are analogous to those described previously.

Aspect (b) of the process in accordance with the invention is an esterification which can be carried out according to methods which are generally usual and which are familiar to any person skilled in the art.

The carboxylic acid to be esterified can be used conveniently in the form of one of its reactive derivatives, for example, in the form of an acid halide (for example, an acid chloride), an imidazolide and the like, which is then reacted with the corresponding hydroxyl compound. In this case, the reactive functional derivative of the carboxylic acid, which can be prepared, for example, by means of thionyl chloride, carbonyldiimidazole and the like, need not be isolated, but can be produced in situ. As reactive functional derivatives of the carboxylic acids to be esterified there can also be used silver salts; the desired ester is obtained from such a silver salt by reaction with a corresponding halide. The reaction conditions such as temperature, duration, solvent and the like vary according to the nature of the reactive carboxylic acid derivative which is used.

Free carboxylic acids can be used, for example, when the esterification is carried out by means of a component containing an olefinic double bond. Thus, a corresponding t-butyl ester is obtained by treating a free carboxylic acid with isobutylene in the presence of a small amount of a strong mineral acid (for example, concentrated sulfuric acid).

In accordance with process aspect (c) in accordance with the invention a carboxylic acid is converted into an amide which is optionally appropriately substituted on the nitrogen atom, which can be effected according to methods which are known and which are familiar to any person skilled in the art.

When a free carboxylic acid is used, then the reaction is effected with a compound of formula IV or with ammonia in the presence of a dehydrating agent such as dicyclohexylcarbodiimide. The reaction is conveniently effected in an organic solvent which is inert under the reaction conditions, for example, in an ether such as tetrahydrofuran and the like, it takes several (for example, 10–20) hours and is conveniently carried out at about room temperature.

As reactive functional derivatives of the carboxylic acids used in this aspect of the process in accordance with the invention there are suitable, for example, their esters, their imidazolides and the like, whereby the imidazolides need not be isolated, but can be produced in situ. The reaction conditions such as solvent, temperature, duration and the like vary depending on the nature of the reactive functional carboxylic acid derivative which is used.

Compounds of formula I in which $R^{10}$ is hydrogen and $R^{11}$ is hydroxy are obtained in accordance with process aspect (d) in accordance with the invention. The reduction is conveniently effected by means of a complex hydride in an organic solvent which is inert under the reaction conditions, for example, by means of sodium borohydride in methanol and the like. The reduction is conveniently effected at about room temperature and takes about 1 to a few hours.

The hydrolysis in accordance with process aspect (e) in accordance with the invention is effected according to methods which are known and which are familiar to any person skilled in the art, conveniently under alkaline conditions, for example, by means of an alkali metal hydroxide such as sodium hydroxide, in water or in a mixture of water and a water-miscible organic solvent such as tetrahydrofuran. It takes about 1 to a few hours and is conveniently effected at about room temperature.

The salt formation in accordance with process aspect (f) in accordance with the invention is effected according to methods which are usual and which are familiar to any person skilled in the art. Basic compounds of formula I can be converted into pharmaceutically acceptable acid addition salts, for example, with hydrogen chloride, hydrogen bromide, phosphoric acid, sulfuric acid, citric acid, p-toluenesulfonic acid and the like. Acidic compounds of formula I can form pharmaceutically acceptable salts with suitable bases, for example, alkali metal salts such as sodium or potassium salts, alkaline earth metal salts such as magnesium or calcium salts as well as salts with amines such as triethanolamine, diethylaminoethanol, triethylamine, trimethylamine, diethylamine and the like.

The starting materials of formula II can be prepared by oxidizing a benzoquinoline derivative of the formula

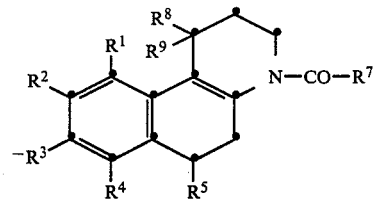

wherein
$R^1$, $R^2$, $R^3$, $R^4$, $R^5$, $R^7$, $R^8$ and $R^9$ have the significance mentioned earlier.

Compounds of formula V can, in turn, be obtained by
(aa) reducing a benzoquinolinone derivative of the formula

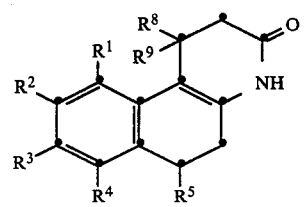

wherein
$R^1$, $R^2$, $R^3$, $R^4$, $R^5$, $R^8$ and $R^9$ have the significance mentioned earlier,
or
(bb) reacting a compound of the formula

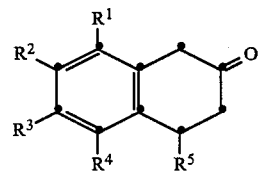

wherein
$R^1$, $R^2$, $R^3$, $R^4$ and $R^5$ have the significance mentioned earlier,
in the presence of a strong base with a compound of the formula

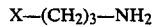

$$X-(CH_2)_3-NH_2 \qquad \text{VIII}$$

wherein
X is a leaving group,
and appropriately N-substituting the compound obtained.

The oxidizing of benzoquinoline derivatives of formula V to corresponding benzazecinediones of formula II is conveniently effected by means of m-chloro-perbenzoic acid in an inert organic solvent, for example, in a halogenated hydrocarbon such as chloroform and the like, conveniently at temperatures of about −20° C. to about 30° C., preferably between about −5° C. and about room temperature.

Furthermore, this oxidation can also be carried out conveniently by means of potassium permanganate and sodium periodate, conveniently in a two-phase system consisting of water and an organic solvent which is not miscible therewith, for example, a halogenated hydrocarbon such as methylene chloride and the like. In this case there is preferably added a phase transfer catalyst, especially a quaternary ammonium salt such as benzyltriethylammonium chloride and the like. Again, the oxidation by means of potassium permanganate/sodium periodate can be carried out conveniently at temperatures between about 0° C. and about 30° C., for example, at about room temperature.

Furthermore, oxidizing agents or oxidation systems such as peracetic acid, hydrogen peroxide and formic acid or p-toluenesulfonic acid, chromic acid, Jones reagent and the like are suitable for carrying out the oxidation in question.

The reduction of a benzoquinolinone derivative of formula VI is conveniently effected by means of a complex hydride such as lithium aluminum hydride and the like in an organic solvent which is inert under the reaction conditions, conveniently in an ether such as tetrahydrofuran, dioxane and the like. The reduction can be effected at temperatures between about room temperature and about 120° C., conveniently at the reflux temperature.

The reaction of a compound of formula VII with a compound of formula VIII is effected in the presence of a strong base, conveniently in the presence of an inorganic base such as potassium or sodium hydroxide, a quaternary ammonium base such as benzyltrimethylammonium hydroxide and the like. The leaving group denoted by the symbol X in formula VIII is conveniently a halogen atom, especially a chlorine atom, but other equivalent leaving groups also come into consideration, for example, alkylsulfonyloxy groups such as mesyloxy, arylsulfonyloxy groups such as benzenesulfonyloxy, p-toluenesulfonyloxy, p-bromobenzenesulfonyloxy and the like. The compound of formula VIII is conveniently used in the form of an acid addition salt, for example, as the hydrochloride. The reaction is effected in the presence of an organic solvent which is inert under the reaction conditions, for example, in an aromatic hydrocarbon such as toluene and the like. The reaction of the compounds of formulas VII and VIII can be effected conveniently at between temperatures of about 30° C. and about 110° C., preferably at the reflux temperature.

Not only in the reduction of a benzoquinolinone derivative of formula VI, but also in the reaction of compounds of formulas VII and VIII, there are obtained compounds which are unsubstituted on the nitrogen and which subsequently must be N-acylated, and for the preparation of compounds of formula II in which $R^7$ is $(C_1-C_4)$-alkyl or $(C_1-C_4)$-alkoxyphenyl there are used as acylating agents reactive derivatives of the corresponding carboxylic acids, conveniently anhydrides such as acetic anhydride, carboxylic acid chlorides such as p-methoxybenzoyl chloride and the like. For the preparation of compounds of formula II in which $R^7$ is amino, the compound which is unsubstituted on the nitrogen can be reacted with α-chloroacetyl isocyanate and the compound obtained can be reacted with hydrazine hydrate. For the preparation of compounds of formula II in which $R^7$ is $(C_2-C_5)$-alkanoyl-amino-$(C_2-C_5)$-alkyl, the compound which is unsubstituted on the nitrogen can be reacted with a phthalimido-$(C_2-C_5)$-alkanoyl halide, the product obtained can be converted by means of hydrazine hydrate into the corresponding free amine and, finally, this can be acylated with a reactive derivative of the corresponding carboxylic acid such as acetyl chloride.

The preparation of compounds of formulas VI and VII is conveniently effected in accordance with the following Reaction Scheme in which $R^1$, $R^2$, $R^3$, $R^4$, $R^5$, $R^8$ and $R^9$ have the significance mentioned earlier and $R^{12}$ and $R^{13}$ each are lower alkyl or together with the nitrogen atom are a heterocyclic residue such as pyrrolin-1-yl, pyrrolidin-1-yl, piperidino, morpholino, 4-$(C_1-C_4$-alkyl)-piperazin-1-yl and the like.

Reaction Scheme

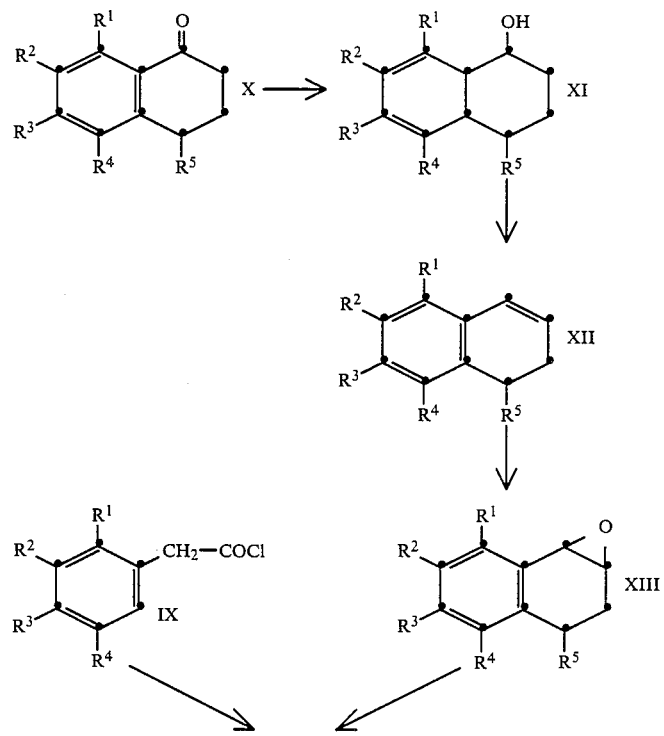

Reaction Scheme

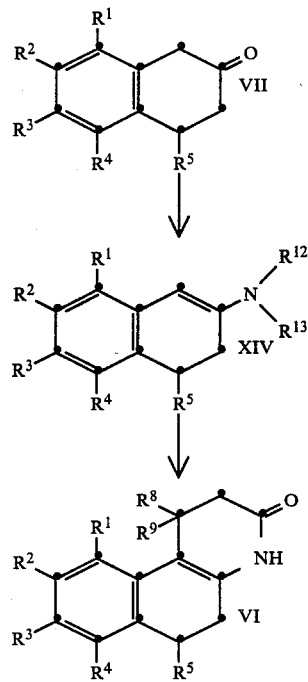

Compounds of formula VII can be prepared in one step from compounds of formula IX by reaction with ethylene or styrene in the presence of aluminum chloride or another Lewis acid which is suitable as a catalyst for such reactions. The reaction is effected in the presence of an organic solvent which is inert under the reaction conditions, conveniently in an halogenated hydrocarbon such as methylene chloride.

Compounds of formula VII can, however, also be prepared by a multi-step synthesis starting from compounds of formula X. First, the compound of formula X is reduced to the corresponding compound of formula XI, conveniently with a complex hydride such as sodium borohydride or the like. The compound of formula XI obtained is then dehydrated to the corresponding compound of formula XII, conveniently under acidic conditions, for example, by means of a strong acid such as p-toluenesulfonic acid or the like in a solvent which is not miscible with water but which distills azeotropically at the reflux temperature, whereby the water which results is removed continuously. The compound of formula XII is then oxidized to the corresponding compound of formula XIII, conveniently by means of m-chloroperbenzoic acid or the like in an organic solvent which is inert under the reaction conditions, for example, in a chlorinated hydrocarbon such as methylene chloride. Compounds of formula VII are then obtained from corresponding compounds of formula XIII, for example, by treatment with an ethereal solution of magnesium bromide or by treatment with an organic sulfonic acid such as p-toluenesulfonic acid or the like in an inert organic solvent such as toluene or the like.

For the preparation of a compound of formula XIV, a corresponding compound of formula VII is reacted with a secondary amine of the formula $HNR^{12}R^{13}$ such as for example, pyrrolidine in the presence of an acid, conveniently an organic sulfonic acid such as p-toluenesulfonic acid or the like, in an organic solvent which is inert under the reaction conditions, for example, in an aromatic hydrocarbon such as benzene; the water which thereby results is removed from the reaction system, for example, by the addition of molecular sieve or by azeotropic distillation. Compounds of formula VI are finally obtained by reacting a corresponding compound of formula XIV with acrylamide, 3,3-dimethylacrylamide or the like. The reaction with acrylamide is conveniently effected in the presence of an acid, for example, an organic sulfonic acid such as p-toluenesulfonic acid, an acidic ion-exchanger or the like, at temperatures of about 100° C. to about 200° C., conveniently of about 100°-150° C., whereby ($C_1$-$C_4$)-alkanols such as ethanol or the like can be used as the solvent. The reaction with 3,3-dimethylacrylamide is conveniently effected in the presence of tetramethoxysilane and caesium fluoride in an aromatic hydrocarbon such as toluene at about the reflux temperature.

As mentioned above, the hydrocinnamic acid derivatives of formula I and their pharmaceutically acceptable salts are compounds with extremely valuable pharmacodynamic properties. They have only a low toxicity, and it has been shown that in the animal experiment described hereinafter they are capable of counteracting cerebral insufficiency produced experimentally.

The test apparatus is a "Skinner box" with an electrifiable grid floor (30×40 cm) and a grey plastic platform (15×15×0.8 cm) in the front right corner. Untrained male rats (100-120 g) are placed individually on the platform. As soon as they climb down on to the grid floor they receive an electric foot-shock (0.8 mA). The normal reaction of untrained rats is thereupon to jump back on to the platform. Since, however, the rats still attempt to climb down again, the foot-shock procedure must by repeated three to five times for each animal. After these three to five repetitions per animal, the rats learn a so-called "passive avoidance response", that is, they no longer attempt to descend to the grid floor, as they know that they are punished when they do so.

Immediately thereafter, three groups each comprising 30 animals are set up. The first group receives an injection (i.p.) of 0.3 mg/kg of scopolamine as well as distilled water (2 ml/kg p.o.). The second group receives an injection (i.p.) of 0.3 mg/kg of scopolamine and an oral dosage of the test substance. The third group receives only distilled water (p.o.).

Two (2) hours later each rat is placed once on the platform in the "Skinner box". The criterion for the assessment of this test for the determination of the effect of a preparation on the short-term memory is whether the animal remains or does not remain for 60 seconds on the platform (the result can thus only read "yes" or "no" for each animal). The statistical significance of the difference between the results obtained in the first and in the second groups is determined by means of the Chi-Square test.

Test results obtained indicate that 70–75% of the animals treated only with distilled water (p.o.) still remember 2–4 hours after learning the "passive avoidance response" that they should remain on the platform. Whereas, 85–92% of the animals treated with scopolamine (0.3 mg/kg i.p.) and distilled water (p.o.) there can be established during 3–4 hours a retrograde effect on the short-term memory, that is, they have forgotten that they must remain on the platform. A substance which is capable of counteracting cerebral insufficiency can reverse the blocking of the short-term memory caused by the injection (i.p.) of 0.3 mg/kg of scopolamine. A dosage of a preparation is denoted as "active" against scopolamine if the number of positive results ("yes") is significantly different from those of control animals treated with scopolamine (0.3 mg/kg i.p.) and only distilled water (p.o.).

In the following Table there are given dosages in which certain compounds of formula I exhibit a significant activity in the test previously described. Moreover, the Table contains data for the acute toxicity ($LD_{50}$ in mg/kg in the case of single oral administration to mice).

TABLE

| $R^1$ | $R^2$ | $R^3$ | $R^4$ | $R^5$ | $R^6$ | $R^7$ | $R^8$ | $R^9$ | $R^{10}$ | $R^{11}$ | Significant active dosage mg/kg p.o. | LD 50 mg/kg p.o. |
|---|---|---|---|---|---|---|---|---|---|---|---|---|
| H | H | Cl | H | H | $NHCH_2COOC_2H_5$ | $CH_3$ | H | H | | Oxo | 0.003<br>0.03<br>0.3<br>3<br>10 | >5000 |
| H | H | Cl | H | H | $OC_2H_5$ | $(CH_2)_3NHCOCH_3$ | H | H | | Oxo | 0.003<br>0.03<br>0.3 | >5000 |
| H | H | Cl | H | H | $NH_2$ | $(CH_2)_3NHCOCH_3$ | H | H | | Oxo | 0.00001<br>0.00003<br>0.0003<br>0.003<br>0.03 | |
| H | H | Cl | H | H | $OCH(CH_3)_2$ | $CH_3$ | H | H | | Oxo | 0.01<br>0.03<br>0.1<br>0.3<br>1<br>3<br>10<br>30 | >4000 |
| H | H | Cl | H | H | $OC_2H_5$ | $CH_3$ | H | H | | Oxo | 0.03<br>0.1<br>0.3<br>1<br>3 | >5000 |
| H | H | Cl | H | H | NH—CH—$COOC_2H_5$<br>\|<br>$(CH_2)$—$COOC_2H_5$ | $CH_3$ | H | H | | Oxo | 0.1<br>0.3<br>3 | >5000 |
| H | H | Cl | H | H | $OCH_2CONH_2$ | $CH_3$ | H | H | | Oxo | 0.03<br>0.3<br>1 | |
| H | H | Cl | H | H | $NH_2$ | $CH_3$ | H | H | | Oxo | 0.03<br>0.3 | >4000 |
| H | H | Cl | H | H | $O—(CH_2)_2—CH_3$ | $CH_3$ | H | H | | Oxo | 0.1<br>0.3 | >5000 |
| H | H | Cl | H | H | $O—(CH_2)_6—CH_3$ | $CH_3$ | H | H | | Oxo | 0.03<br>0.1<br>0.3<br>3 | >5000 |

The compounds of formula I and their pharmaceutically acceptable salts can be used as medicaments, for example, in the form of pharmaceutical preparations. The pharmaceutical preparations can be administered orally, for example, in the form of tablets, coated tablets, dragees, hard and soft gelatin capsules, solutions, emulsions or suspensions. The administration can, however, also be effected rectally, for example, in the form of suppositories, or parenterally, for example, in the form of injection solutions.

As mentioned earlier, medicaments containing a compound of formula I or a pharmaceutically usable salt thereof are also an object of the invention, as is a process for the preparation of such medicaments which comprises bringing one or more compounds of formula I and/or pharmaceutically acceptable salts thereof and, if desired, one or more other therapeutically active substances into a galenical administration form together with one or more therapeutically inert excipients.

For the preparation of tablets, coated tablets, dragees and hard gelatin capsules there can be used as excipients, for example, lactose, maize starch or derivatives thereof, talc, stearic acid or its salts and the like.

For soft gelatin capsules there are suitable as excipients for example, vegetable oils, waxes, fats, semi-solid and liquid polyols and the like.

For the preparation of solutions and syrups there are suitable as excipients, for example, water, polyols, saccharose, invert sugar, glucose and the like.

For injection solutions there are suitable as excipients, for example, water, alcohols, polyols, glycerine, vegetable oils and the like.

For suppositories, there are suitable as excipients, for example, natural or hardened oils, waxes, fats, semi-liquid or liquid polyols and the like.

The pharmaceutical preparations can contain, in addition, preserving agents, solubilizers, stabilizing agents, wetting agents, emulsifying agents, sweetening agents, coloring agents, flavoring agents, salts for varying the osmotic pressure, buffers, coating agents or antioxidants. They can also contain other therapeutically valuable substances.

In accordance with the invention the compounds of formula I and pharmaceutically acceptable salts thereof can be used in the control or prevention of cerebral insufficiency or in the improvement of cognitive functions (such as memory capacity, learning capability, interest in the surroundings and self-care), for example, in geriatrics, in the case of intoxications such as alcoholism and in the case of cerebro-vascular disorders; further possible fields of use are vestibular disorders (such as Meniere's disease) and development disorders (such as dyslexia). The dosage can vary within wide limits and will, of course, be fitted to the individual requirements in each particular case. In general, in the case of oral administration a daily dosage of about 1 to 2500 mg should be appropriate, however, the upper limit just mentioned can be exceeded when this is shown to be indicated.

Finally, the use of the compounds of formula I and of pharmaceutically acceptable salts thereof for the preparation of medicaments for the control or prevention of cerebral insufficiency or for the improvement of cognitive functions is also an object of the invention.

The following Examples, further illustrate the invention. All temperatures are given in degrees Celsius, unless otherwise stated.

EXAMPLE 1

(a) 1155 g (6.4 mol) of 6-chloro-3,4-dihydro-2(1H)-naphthalenone are dissolved in 5 l of toluene, 500 g (7.0 mol) of pyrrolidine and subsequently a solution of 26 g (0.14 mol) of p-toluenesulfonic acid monohydrate in toluene are added dropwise thereto and the mixture is boiled under reflux on a water separator. When about 120 ml of water have separated, 4 l of toluene are distilled and the mixture is left to cool slowly. A solid thereby crystallizes out. Filtration and washing with acetone gives 1-(6-chloro-3,4-dihydro-2-naphthyl)-pyrrolidine with melting point 117°–118°. Concentration of the mother liquor, suspension of the residue in ether, exfiltration and washing with acetone gives an additional portion of the above product with melting point 117°–118°.

(b) 701 g (3 mol) of 1-(6-chloro-3,4-dihydro-2-naphthyl)-pyrrolidine and 640 g (19 mol) of acrylamide in 7 ml of ethanol are boiled under reflux for 3 days with the addition of 70 g of Amberlite IR200. The separated solid is removed by filtration, extractively crystallized with dioxane and there is obtained 8-chloro-1,4,5,6-tetrahydrobenzo[f]-quinolin-3(2H)-one with melting point 228°–230° C.

(c) 147 g (1.94 mol) of lithium aluminum hydride are suspended in 4 l of tetrahydrofuran under argon, 454 g (1.94 mol) of 8-chloro-1,4,5,6-tetrahydrobenzo[f]quinolin-3(2H)-one are slowly added thereto and the mixture is boiled under reflux for 2.5 hours. The mixture is then cooled and 470 ml of 18 percent sodium hydroxide solution are added thereto. The resulting mixture is stirred at room temperature for 30 minutes, filtered and the filter residue is washed with tetrahydrofuran. Upon evaporation of the filtrate, there is obtained 8-chloro-1,2,3,4,5,6-hexahydrobenzo[f]quinoline as a yellow oil.

(d) 229 g (1.04 mol) of 8-chloro-1,2,3,4,5,6-hexahydrobenzo[f]quinoline are dissolved in 2 ml of methylene chloride, treated with 115 g (1.14 mol) of triethylamine and 89.5 g (1.14 mol) of acetyl chloride in 400 ml of methylene chloride are added dropwise thereto at 0°. After stirring at room temperature for 1 hour, the mixture is poured into water, extracted with methylene chloride and the methylene chloride phase is dried with magnesium sulfate. Distillation of the solvent in a vacuum gives a crude product which is suspended in 500 ml of ether and removed by filtration. There is obtained 4-acetyl-8-chloro-1,2,3,4,5,6-hexahydrobenzo[f]quinoline with melting point 106°–108°. Concentration of the mother liquor and chromatography (silica gel/-chloroform) gives an additional portion with melting point 106°–108°.

4-Acetyl-8-chloro-1,2,3,4,5,6-hexahydrobenzo[f]quinoline can also be prepared from 6-chloro-3,4-dihydro-2(1H)-napthalenone as follows:

100 g (0.55 mol) of 6-chloro-3,4-dihydro-2(1H)-naphthalenone are dissolved under argon in 2 l of toluene, treated with 64.0 g of powdered potassium hydroxide, heated to boiling temperature, 165 g of 3-chloropropylamine hydrochloride are added portionwise thereto during 30 minutes and the mixture is boiled on a water separator until educt can no longer be detected in the thin-layer chromatogram. After cooling to room temperature, the mixture is treated with 155 ml of triethylamine. While cooling with ice so that an internal temperature of 25° is not exceeded, the mixture is treated dropwise with 60 ml of acetyl chloride dissolved in 450 ml of toluene. The mixture is stirred at room temperature for 1 hour, extracted with water/-methylene chloride and dried with magnesium sulfate. The solvent is distilled in a vacuum and there is obtained 4-acetyl-8-chloro-1,2,3,4,5,6-hexahydrobenzo[f]quinoline in the form of brown crystals which can be used as the crude product for the reaction described hereinafter.

(e) 115 g (0.44 mol) of 4-acetyl-8-chloro-1,2,3,4,5,6-hexahydrobenzo[f]quinoline are dissolved in 1 l of methylene chloride and a suspension of 189 g (0.93 mol) of m-chloroperbenzoic acid (85%) in 500 ml of methylene chloride is added dropwise thereto at 0°. After stirring at room temperature for 1 hour, the precipitate formed is removed by filtration and the filtrate is extracted with 2N sodium hydroxide solution and with water. Drying of the organic phase with magnesium sulfate, distillation of the solvent in vacuo and recrystallization of the residue from ethyl acetate-ether gives 4-acetyl-11-chloro-1,2,3,4,5,6,7-hexahydro-4-benzazecine-3,8-dione as white crystals with melting point 154°–156°.

(f) 1 ml of concentrated hydrochloric acid is added to a solution of 4.00 g (0.014 mol) of 4-acetyl-11-chloro-1,2,4,5,6,7-hexahydro-4-benzazecine-4,8-dione in 200 ml of methanol and the mixture is stirred at room temperature for 20 hours. The solution is concentrated, extracted with methylene chloride/water, dried with magnesium sulfate and the solvent is distilled in a vacuum. Chromatography on silica gel with ethyl acetate and then on aluminum oxide with ethyl acetate and crystallization from t-butyl methyl ether gives methyl 2-(4-acetamidobutyryl)-5-chlorohydrocinnamate as white crystals with melting point 46°–48°.

EXAMPLE 2

5 ml of concentrated hydrochloric acid are added to a solution of 4.00 g (0.014 mol) of 4-acetyl-11-chloro-1,2,4,5,6,7-hexahydro-4-benzazecine-3,8-dione in 250 ml of ethanol and the mixture is stirred at room temperature for 30 hours. The solution is concentrated, extracted with methylene chloride/water, dried with magnesium sulfate and the solvent is distilled in a vacuum. Chromatography on silica gel with ethyl acetate-hexane (2:1) and crystallization from ether gives ethyl 2-(4-acetamidobutyryl)-5-chloro-hydrocinnamate as beige crystals with melting point 64°–66°.

EXAMPLE 3

10 ml of concentrated hydrochloric acid are added to a solution of 7.35 g (0.025 mol) of 4-acetyl-11-chloro-1,2,4,5,6,7-hexahydro-4-benzazecine-3,8-dione in 400 ml of n-propanol and the mixture is stirred at room temperature for 24 hours. The solution is concentrated, extracted with methylene chloride/water, dried with magnesium sulfate and the solvent is distilled in a vacuum. Chromatography on silica gel with ethyl acetate-hexane (2:1) and crystallization from ethyl acetate-hexane gives propyl 2-(4-acetamidobutyryl)-5-chlorohydrocinnamate as white crystals with melting point 60°–62°.

EXAMPLE 4

5 ml of concentrated hydrochloric acid are added to a solution of 4.00 g (0.014 mol) of 4-acetyl-11-chloro-1,2,4,5,6,7-hexahydro-4-benzazecine-3,8-dione in 250 ml of isopropanol and the mixture is stirred at room temperature for 24 hours. The solution is concentrated, extracted with methylene chloride/water, dried with magnesium sulfate and the solvent is distilled in a vacuum..Chromatography on silica gel with ethyl acetate-hexane (2:1) and crystallization from ether gives isopropyl 2-(4-acetamidobutyryl)-5-chlorohydrocinnamate as white crystals with melting point 35°–37°.

EXAMPLE 5

15 ml of concentrated hydrochloric acid are added to a solution of 10.00 g (0.034 mol) of 4-acetyl-11-chloro-1,2,4,5,6,7-hexahydro-4-benzazecine-3,8-dione in 70 ml of n-butanol and 50 ml of methylene chloride and the mixture is stirred at room temperature for 18 hours. The solution is concentrated, extracted with methylene chloride/water, dried with magesium sulfate and the solvent is distilled in a vacuum. Chromatography on silica gel with ethyl acetate and crystallization from ether gives butyl 2-(4-acetamidobutyryl)-5-chlorohydrocinnamate as white crystals with melting point 56°–57°.

EXAMPLE 6

15 ml of concentrated hydrochloric acid are added to a solution of 10.00 g (0.034 mol) of 4-acetyl-11-chloro-1,2,4,5,6,7-hexahydro-4-benzazecine-3,8-dione in 90 ml of n-nonanol and 50 ml of methylene chloride and the mixture is stirred at room temperature for 15 hours. The solution is concentrated, extracted with methylene chloride/water, dried with magnesium sulfate and the solvent is distilled in a vacuum. Chromatography on silica gel with ethyl acetate-hexane (4:1) and crystallization from ether gives nonyl 2-(4-acetamidobutyryl)-5-chlorohydrocinnamate as white crystals with melting point 55°–57°.

EXAMPLE 7

15 ml of concentrated hydrochloric acid are added to a solution of 10.00 g (0.034 mol) of 4-acetyl-11-chloro-1,2,4,5,6,7-hexahydro-4-benzazecine-3,8-dione in 90 ml of 5-nonanol and 50 ml of methylene chloride and the mixture is stirred at room temperature for 18 hours. The solution is concentrated, extracted with methylene chloride/water, dried with magnesium sulfate and the solvent is distilled in a vacuum. Chromatography on silica gel with ethyl acetate gives 1-butylpentyl 2-(4-acetamido-butyryl)-5-chlorohydrocinnamate as a yellow oil.

EXAMPLE 8

(a) 31.4 g (0.143 mol) of 8-chloro-1,2,3,4,5,6-hexahydrobenzo[f]quinoline dissolved in 300 ml of methylene chloride are added at 0° to a solution of 36.0 g (0.143 mol) of 4-phthalimidobutyryl chloride in 360 ml of methylene chloride and the mixture is stirred at room temperature for 1 hour. The solution is concentrated, extracted with methylene chloride and aqueous sodium hydrogen carbonate solution, dried with magnesium sulfate and the solvent is distilled in a vacuum. Extractive crystallization with acetone gives 8-chloro-1,2,3,4,5,6-hexahydro-4-(4-phthalimidobutyryl)benzo[f]quinoline as white crystals with melting point 182°–183°.

(b) A suspension of 10.9 g (0.025 mol) of 8-chloro-1,2,3,4,5,6-hexahydro-4-(4-phthalimidobutyryl)benzo[f]-quinoline and 3.2 ml (0.065 mol) of hydrazine hydrate in 150 ml of ethanol is boiled at reflux temperature for 2 hours. The solution is concentrated, extracted with methylene chloride/water, dried with sodium sulfate and the solvent is distilled in a vacuum. The residue is dissolved in 10 ml of 5.5N methanolic hydrochloric acid and precipitated with ether. Recrystallization from methanol/ether gives 4-(4-aminobutyryl)-8-chloro-1,2,3,4,5,6-hexahydrobenzo[f]quinoline hydrochloride as beige crystals with melting point 225°.

(c) To a suspension of 5.09 g (0.015 mol) of 4-(4-aminobutyryl)-8-chloro-1,2,3,4,5,6-hexahydrobenzo[f]quinoline in 50 ml of methylene chloride are added 5 ml (0.036 mol) of triethylamine and then at 0° 1.33 ml (0.019 mol) of acetyl chloride dissolved in 15 ml of methylene chloride, and the mixture is stirred at room temperature for 1 hour. Then, the mixture is extracted with methylene chloride/water, dried with magnesium sulfate and the solvent is distilled in a vacuum. Crystallization from methylene chloride/ether, chromatography on silica gel with ethyl acetate/methanol (9:1) and renewed crystallization from methylene chloride/ether gives N-[4-[8-chloro-2,3,5,6,-tetrahydrobenzo[f]quinolin-4(1H)-yl]-4-oxobutyl]acetamide as white crystals with melting point 142°–143°.

(d) 4.80 g (0.024 mol) of 85 percent m-chloroperbenzoic acid dissolved in 50 ml of methylene chloride are added at 0° to a solution of 4.00 g (0.016 mol) of N-[4-[8-chloro-2,3,5,6,7-tetrahydrobenzo[f]quinolin-4(1H)-yl]-4-oxobutyl]-acetamide in 40 ml of methylene chloride and the mixture is stirred at room temperature for 1 hour. Then, the mixture is extracted with methylene chloride/water, dried with magnesium sulfate and the solvent is distilled in a vacuum. Chromatography on silica gel with ethyl acetate/methanol (9:1) and crystallization from ethyl acetate/hexane gives N-[3-[(11-chloro-2,3,5,6,7,8-hexahydro-3,8-dioxo-4-benzazecin-4-(1H)-yl)carbonyl]propyl]acetamide as white crystals with melting point 135°–136°.

(e) 1 ml of concentrated hydrochloric acid is added to a solution of 2.66 g (0.007 mol) of N-[3-[(11-chloro-2,3,5,6,7,8-hexahydro-3,8-dioxo-4-benzazecin-4-(1H)-yl)carbonyl]propyl]acetamide in 100 ml of ethanol and 30 ml of methylene chloride and the mixture is stirred at room temperature for 5 days. The solution is concentrated, extracted with methylene chloride/water, dried with magnesium sulfate and the solvent is distilled in a vacuum. Chromatography on aluminum oxide with ethyl acetate/ethanol (19:1) and crystallization from methylene chloride/ether gives ethyl 2-[4-(4-acetamidobutyramido)butyryl]-5-chlorohydrocinnamate as white crystals with melting point 95°.

EXAMPLE 9

(a) 15.0 g (0.06 mol) of 8-chloro-1,2,3,4,5,6-hexahydrobenzo[f]quinoline are dissolved in 150 ml of methylene chloride, treated with 6.68 g (0.066 mol) of triethylamine and 11.2 g (0.066 mol) of p-methoxybenzoyl chloride in 50 ml of methylene chloride are added dropwise thereto at 0°. After stirring at room temperature for 1 hour, the mixture is extracted with water, dried with magnesium sulfate and the solvent is distilled in a vacuum. Crystallization (methylene chloride-ether) gives 4-(p-methoxybenzoyl)-8-chloro-1,2,3,4,5,6-hexahydrobenzo-[f]quinoline as white crystals with melting point 182°–183°.

(b) 8.80 g (0.025 mol) of 4-(p-methoxybenzoyl)-8-chloro-1,2,3,4,5,6-hexahydrobenzo[f]quinoline are dissolved in 100 ml of chloroform and a suspension of 10.3 g (0.051 mol) of 85% m-chloroperbenzoic acid in 100 ml of chloroform is added dropwise thereto at 0°. After stirring at room temperature for 1 hour, the mixture is extracted with 2N sodium hydroxide solution and water, dried with magnesium sulfate and the solvent is distilled in a vacuum. Chromatography (silica gel, ether-hexane, 2:1) and crystallization (ether-hexane) gives 4-(p-methoxybenzoyl)-11-chloro-1,2,4,5,6,7-hexahydro-4-benzazecine-3,8-dione as white crystals with melting point 143°.

(c) 5 ml of concentrated hydrochloric acid are added to a solution of 3.60 g (0.009 mol) of 4-(p-methoxybenzoyl)-11-chloro-1,2,4,5,6,7-hexahydro-4-benzazecine-3,8-dione in 200 ml of methanol and 50 ml of methylene chloride and the mixture is stirred at room temperature for 60 hours. The solution is concentrated, extracted with methylene chloride/water, dried with magnesium sulfate and the solvent is distilled in a vacuum. Chromatography on silica gel with hexane-ethyl acetate (1:1) and crystallization from methylene chloride/hexane gives methyl 2-[4-(p-methoxybenzoyl)amidobutyryl]-5-chlorohydrocinnamate as white crystals with melting point 111°.

EXAMPLE 10

500 ml of 2N hydrochloric acid are added to a solution of 103 g (0.35 mol) of 4-acetyl-11-chloro-1,2,4,5,6,7-hexahydro-4-benzazecine-3,8-dione in 1 l of tetrahydrofuran and the mixture is stirred at room temperature overnight. The mixture is concentrated in a vacuum, treated with methylene chloride and extracted twice with 2N sodium hydroxide solution; the aqueous phase is then acidified with 6N hydrochloric acid and extracted with methylene chloride. Removal of the solvent by distillation in a vacuum and chromatography on silica gel with methylene chloride/methanol (20:1) yields 2-(4-acetamidobutyryl)-5-chlorohydrocinnamic acid with melting point 90°–92°.

EXAMPLE 11

(a) 154.8 g of 2-chloro-phenylacetyl chloride dissolved in 290 ml of methylene chloride are added dropwise within 1 hour to 218 g of aluminum chloride in 1000 ml of methylene chloride while stirring at between 0° and 5°. Thereafter, ethylene is introduced at 0° and 5° over 40 minutes. The mixture is stirred at room temperature for 1 hour and treated at between 0° and 5° with 570 ml of water. The methylene chloride phase is washed with 2×500 ml of 2N hydrochloric acid, 2×500 ml of sodium hydrogen carbonate solution and 700 ml of water, dried with sodium sulfate and concentrated in a vacuum. The 8-chloro-3,4-dihydro-2(1H)-naphthalenone, crystallized from 400 ml of low-boiling petroleum ether, exhibits a melting point of 56°–59°.

(b) 70.0 g of 8-chloro-3,4-dihydro-2(1H)-naphthalenone are boiled at reflux for 2.5 hours in 550 ml of benzene and 33 ml of pyrrolidine in the presence of 1.4 g of p-toluenesulfonic acid. The crude 1-(8-chloro-3,4-dihydro-2-naphthyl)-pyrrolidine obtained is processed without purification.

(c) 56.0 g of acrylamide and 3.0 g of anhydrous p-toluenesulfonic acid are added to 89.4 g of crude 1-(8-chloro-3,4-dihydro-2-naphthyl)-pyrrolidine. The mixture is heated under nitrogen at 100° for 2 hours and at 150° for 2 hours, extracted with methylene chloride-water and filtered through 500 g of silica gel and the solvent is distilled in a vacuum. The 10-chloro-1,4,5,6-tetrahydrobenzo[f]quinolin-3(2H)-one obtained exhibits a melting point of 186°–187° after recrystallization from ethyl acetate.

(d) 20.0 g of 10-chloro-1,4,5,6-tetrahydrobenzo[f]quinolin-3(2H)-one are added portionwise within 35 minutes at 20° to 25° to a stirred suspension of 6.49 g of lithium aluminum hydride in 240 ml of dry tetrahydrofuran. The reaction mixture is subsequently boiled under reflux for 150 minutes. The mixture is cooled, treated at 0° to 10° with 21.0 ml of 6.5N sodium hydroxide solution, filtered and rinsed several times with 20 ml of tetrahydrofuran each time. Distillation of the solvent in a vacuum gives 10-chloro-1,2,3,4,5,6-hexahydrobenzo[f]quinoline which is processed directly.

(e) 20.1 g of crude 1-chloro-1,2,3,4,5,6-hexahydrobenzo[f]quinoline are dissolved in 40 ml of pyridine and 36 ml of acetic anhydride. The reaction mixture is left to stand at room temperature for 20 hours, evaporated, the residue remaining behind is taken up twice in 150 ml of dry toluene each time and the solutions obtained are evaporated to dryness. Chromatography of the residue on silica gel with chloroform yields 4-acetyl- 10-chloro-1,2,3,4,5,6-hexahydrobenzo[f]quinoline which exhibits a melting point of 117°–118° after recrystallization from isopropyl ether.

(f) 16.0 g of 85 percent m-chloroperbenzoic acid in 205 ml of chloroform are added at 0° to 5° to a solution of 8.50 g of 4-acetyl-10-chloro-1,2,3,4,5,6-hexahydrobenzo[f]quinoline in 205 ml of chloroform. After stirring at room temperature for 4 hours, the mixture is treated with 4 g of potassium iodide and 70 ml of water and with sodium thiosulfate until decolorization occurs. The chloroform phase is washed with 70 ml of 2N sodium hydroxide solution and twice with 170 ml of water and evaporated in a vacuum. Chromatography on 100 g of silica gel with methylene chloride yields 4-acetyl-9-chloro-1,2,4,5,6,7-hexahydro-4-benzazecine-3,8-dione with a melting point of 115°–116° after recrystallization from isopropyl ether.

(g) 1 ml of 25 percent hydrochloric acid is added to a solution of 5.00 g (0.017 mol) of 4-acetyl-9-chloro-1,2,4,5,6,7-hexahydro-4-benzazecine-3,8-dione in 153 ml of methanol and the mixture is stirred at room temperature for 4 days. The solution is concentrated, extracted with methylene chloride and aqueous sodium hydrogen carbonate solution, dried with sodium sulfate and the solvent is distilled in a vacuum. Chromatography on silica gel with methylene chloride and then with ethyl acetate and crystallization from petroleum ether gives methyl 2-(4-acetamidobutyryl)-3-chloro-hydrocinnamate as white crystals with melting point 51°–52°.

EXAMPLE 12

(a) 149.4 g of 4-fluorophenylacetyl chloride in 300 ml of methylene chloride are added within 60 minutes to 230 g of aluminum chloride in 1050 ml of methylene chloride while stirring between 0° and 5°. Ethylene is conducted in at 0° to 5° for 30 minutes, the mixture is stirred at room temperature for an additional hour and treated at 0° to 5° within 30 minutes with 600 ml of ice-water. The methylene chloride phase is washed with 2N hydrochloric acid, water and saturated sodium hydrogen carbonate solution, dried with sodium sulfate and the solvent is distilled off in a vacuum. The residue is treated with 250 ml of low-boiling petroleum ether, left to stand in a refrigerator overnight and the 6-fluoro-3,4-dihydro-2(1H)-naphthalenone with melting point 50°–60° is removed by filtration.

(b) 16.7 g of 6-fluoro-3,4-dihydro-2(1H)-naphthalenone in 200 ml of benzene are boiled at reflux for 2.5 hours with 8.4 ml of pyrrolidine and 0.35 g of anhydrous p-toluenesulfonic acid. The 1-(6-fluoro-3,4-dihydro-2-naphthyl)pyrrolidine obtained is treated, without purification, with 10.8 g of acrylamide and 0.5 g of p-toluenesulfonic acid. The mixture is heated under nitrogen at 100° for 2 hours and at 150° for 2 hours. The mixture is dissolved in 180 ml of chloroform, washed with water and chromatographed over 150 g of silica gel with chloroform. Recrystallization from ethyl acetate gives 8-fluoro-1,4,5,6-tetrahydrobenzo[f]quinolin-3(2H)-one with melting point 223°–224°.

(c) 6.20 g of 8-fluoro-1,4,5,6-tetrahydrobenzo[f]quinolin-3(2H)-one are added portionwise under nitrogen within 35 minutes at 20° to 25° to a stirred suspension of 2.17 g of lithium aluminum hydride in 60 ml of dry tetrahydrofuran. The reaction mixture is boiled for 150 minutes under reflux and then treated at 0° to 10° with 7.0 ml of 6.5N sodium hydroxide solution. The mixture is filtered, rinsed several times with 20 ml of tetrahydrofuran each time and the solvent is distilled in a vacuum. The thus-obtained 8-fluoro-1,2,3,4,5,6-hexahydrobenzo[f]quinoline obtained is processed directly.

(d) A solution of 6.00 g of crude 8-fluoro-1,2,3,4,5,6-hexahydrobenzo[f]quinoline in 13 ml of pyridine and 12 ml of acetic anhydride is left to stand at room temperature for 20 hours and evaporated. The residue remaining behind is taken up twice in 50 ml of dry toluene each time and the solutions obtained are evaporated to dryness. The residue is chromatographed on 150 g of silica gel with methylene chloride. The 4-acetyl-8-fluoro-1,2,3,4,5,6-hexahydrobenzo[f]quinoline obtained exhibits a melting point of 101°–102° after recrystallization from isopropyl ether.

(e) 2.48 g of 4-acetyl-8-fluoro-1,2,3,4,5,6-hexahydrobenzo[f]quinoline in 60 ml of chloroform are treated at 0° to 5° with 5.24 g of 85 percent m-chloroperbenzoic acid in 40 ml of chloroform and the mixture is stirred at room temperature for 3 hours. Then 1.10 g of potassium iodide and 15 ml of water are then added thereto and sodium thiosulfate is added until decolorization occurs. The chloroform phase is separated and washed with 15 ml of 2N sodium hydroxide solution and 2×40 ml of water. Distillation of the chloroform in a vacuum and recrystallization from ethyl acetate yields 4-acetyl-11-fluoro-1,2,4,5,6,7-hexahydro-4-benzazecine-3,8-dione with a melting point of 161°–162°.

(f) 20 ml of 2N hydrochloric acid are added to a solution of 3.00 g (0.011 mol) of 4-acetyl-11-fluoro-1,2,4,5,6,7-hexahydro-4-benzazecine-3,8-dione in 40 ml of acetonitrile and the mixture is stirred at room temperature for 65 hours. Concentration of the solution, chromatography on silica gel with tetrahydrofuran and crystallization from ether gives 2-(4-acetamidobutyryl)-5-fluorohydrocinnamic acid as white crystals with melting point 100°–101°.

EXAMPLE 13

0.75 ml of 25 percent hydrochloric acid is added to a solution of 5.00 g (0.018 mol) of 4-acetyl-11-fluoro-1,2,4,5,6,7-hexahydro-4-benzazecine-3,8-dione in 163 ml of methanol and the mixture is stirred at room temperature for 99 hours. The solution is concentrated, extracted with toluene and saturated sodium hydrogen carbonate solution, dried with sodium sulfate and the solvent is distilled in a vacuum. Chromatography on silica gel with chloroform/ethyl acetate and then on aluminum oxide with methylene chloride/ethyl acetate and subsequent trituration in petroleum ether gives methyl 2-(4-acetamidobutyryl)-5-fluorohydrocinnamate as light yellow crystals with melting point 39°–40°.

EXAMPLE 14

(a) 12.0 g of 6-methoxy-2-tetralone in 200 ml of benzene are boiled at reflux for 2 hours with 5.6 ml of pyrrolidine in the presence of 0.5 g of anhydrous p-toluenesulfonic acid. The toluene is removed in a vacuum. 9.70 g of acrylamide and 0.5 g of p-toluene-sulfonic acid are added to the crude 1-(6-methoxy-3,4-dihydro-2-naphthyl)pyrrolidine obtained. The mixture is heated under nitrogen at 100° for 2 hours and at 150° for 2 hours, extracted with chloroform/water, dried with sodium sulfate and the solvent is distilled in a vacuum. Chromatography on 160 g of silica gel with methylene chloride and recrystallization from ethyl acetate gives 8-methoxy-1,4,5,8-tetrahydrobenzo[f]-quinolin-3(2H)-one with melting point 208°–209°.

(b) 5.10 g of 8-methoxy-1,4,5,8-tetrahydrobenzo[f]-quinolin-3(2H)-one are added portionwise at 20° under nitrogen within 35 minutes to a stirred suspension of 1.69 g of lithium aluminum hydride in 50 ml of dry tetrahydrofuran. The reaction mixture is boiled under reflux for 150 minutes and treated at 0° to 10° with 1.5 ml of 6.5N sodium hydroxide solution. The mixture is filtered, rinsed several times with tetrahydrofuran and the solvent is distilled in a vacuum. The thus-obtained 8-methoxy-1,2,3,4,5,6-hexahydrobenzo[f]quinoline is processed directly.

(c) A mixture of 4.70 g of 8-methoxy-1,2,3,4,5,6-hexahydrobenzo[f]-quinoline in 15 ml of pyridine and 11 ml of acetic anhydride is left to stand at room temperature for 20 hours and evaporated. The residue remaining behind is taken up twice in 50 ml of dry toluene each time and the solutions obtained are evaporated to dryness. The residue is chromatographed on 50 g of silica gel with methylene chloride and gives 4-acetyl-8-methoxy-1,2,3,4,5,6-hexahydrobenzo[f]quinoline with a melting point of 119°-120° after recrystallization from ispropyl ether.

(d) 38.0 g of 85 percent m-chloroperbenzoic acid in 250 ml of chloroform are added dropwise at 0° to 5° to a solution of 21.3 g of 4-acetyl-8-methoxy-1,2,3,4,5,6-hexahydrobenzo[f]quinoline in 200 ml of chloroform and the mixture is stirred at room temperature for 18 hours. The mixture is treated with sodium iodide and water and thereafter with sodium thiosulfate until decolorization occurs. The chloroform phase is washed with aqueous ammonia and sodium chloride solution, dried with sodium sulfate and evaporated in a vacuum. There is obtained 4-acetyl-11-methoxy-1,2,4,5,6,7-hexahydro-4-benzazecine-3,8-dione with a melting point of 156°-158° after recrystallization from ethyl acetate.

(e) 5 ml of concentrated hydrochloric acid are added to a solution of 5.50 g (0.019 mol) of 4-acetyl-11-methoxy-1,2,4,5,6,7-hexahydro-4-benzazecine-3,8-dione in 150 ml of ethanol and the mixture is stirred at room temperature overnight. The solution is concentrated, extracted with methylene chloride/water, dried with magnesium sulfate and the solvent is distilled in a vacuum. Chromatography on silica gel with ethyl acetate and crystallization from ethyl acetate/ether gives ethyl 2-(acetamidobutyryl)-5-methoxyhydrocinnamate as white crystals with melting point 59°-61°.

EXAMPLE 15

(a) 9.00 g (0.042 mol) of 6,7-dichloro-3,4-dihydro-2(1H)-naphthalenone and 0.3 g of p-toluenesulfonic acid are dissolved in 200 ml of pyridine, 3.5 ml (0.042 mol) of pyrrolidine are added dropwise and the mixture is boiled under reflux for 2 hours. Distillation of the solvent in a vacuum, addition of 200 ml of ether and filtering off the crystals formed yields 1-(6,7-dichloro-3,4-dihydro-2naphthyl)pyrrolidine with melting point 141°-142°.

(b) A melt of 10.1 g (0.038 mol) of 1-(6,7-dichloro-3,4-dihydro-2-naphthyl)pyrrolidine, 5.36 g (0.075 mol) of acrylamide and 0.3 g of p-toluenesulfonic acid is stirred under nitrogen at 100° for 2 hours and at 150° for 2 hours. Recrystallization of the melt cake from ethanol yields 8,9-dichloro-1,4,5,6-tetrahydrobenzo[f]quinolin-3(2H)-one with melting point 260°-261°.

(c) 1.57 g (0.042 mol) of lithium aluminum hydride are suspended in 60 ml of tetrahydrofuran under argon, 5.56 g (0.021 mol) of 8,9-dichloro-1,4,5,6-tetrahydrobenzo[f]-quinolin-3(2H)-one are slowly added thereto and the mixture is boiled under reflux for 2.5 hours. The mixture is then cooled to 0°, 5.2 ml of 18 percent sodium hydroxide solution are added dropwise thereto and the precipitate formed is removed by filtration. On evaporation of the filtrate, there is obtained 8,9-dichloro-1,2,3,4,5,6-hexahydrobenzo[f]quinoline as a yellow oil which is processed directly.

(d) 6.17 g (0.024 mol) of 8,9-dichloro-1,2,3,4,5,6-hexahydrobenzo[f]quinoline are dissolved in 10 ml of pyridine, 9 ml (0.09 mol) of acetic anhydride are added dropwise thereto and the mixture is stirred at room temperature for 17 hours. Chromatography on silica gel with chloroform yields a product which is suspended in ether and removed by filtration. There is obtained 4-acetyl-8,9-dichloro-1,2,3,4,5,6-hexahydrobenzo[f]quinoline with melting point 146°-148°.

(e) 4.14 g (0.014 mol) of 4-acetyl-8,9-dichloro-1,2,3,4,5,6-hexahydrobenzo[f]quinoline are dissolved in 70 ml of chloroform and a suspension of 7.28 g (0.036 mol) of m-chloroperbenzoic acid (85 percent) in 100 ml of chloroform is added dropwise thereto at 0°. After stirring at room temperature for 3 hours, the mixture is removed by filtration from the precipitate formed and extracted with potassium iodide and sodium thiosulfate solution. Chromatography on silica gel with chloroform and recrystallization from isopropyl ether gives 4-acetyl-10,11-dichloro-1,2,4,5,6,7-hexahydro-4-benzazecine-3,8-dione as white crystals with melting point 163°-165°.

(f) 2 of concentrated hydrochloric acid are added to a solution. of 1.75 g (0.005 mol) of 4-acetyl-10,11-dichloro-1,2,4,5,6,7-hexahydro-4-benzazecine-3,8-dione in 60 ml of ethanol and the mixture is stirred at room temperature for 20 hours. The solution is concentrated, extracted with methylene chloride/water, dried with magnesium sulfate and the solvent is distilled in a vacuum. Chromatography on silica gel with methylene chloride and crystallization from t-butyl ether gives ethyl 2-(4-acetamidobutyryl)-4,5-dichloro-hydrocinnamate as white crystals with melting point 63°-65°.

EXAMPLE 16

(a) A suspension of 127 g (0.7 mol) of 6-chloro-2-tetralone, 70.0 g (0.7 mol) of 3,3-dimethylacrylamide, 63.6 ml (0.42 mol) of tetramethoxysilane and 85.3 g (0.56 mol) of cesium fluoride in 400 ml of toluene is boiled under reflux for 18 hours. Distillation of the solvent in a vacuum, extraction with methylene chloride/water, chromatography on silica gel with ethyl acetate/hexane (1:1) and recrystallization from methylene chloride/hexane yields 8-chloro-1,1-dimethyl-1,2,5,6-tetrahydrobenzo[f]-quinolin-3-one as white crystals with melting point 213°.

(b) 3.36 g (0.089 mol) of lithium aluminium hydride are suspended in 100 ml of tetrahydrofuran under argon, 11.6 g (0.044 mol) of 8-chloro-1,1-dimethyl-1,2,5,6-tetrahydrobenzo[f]quinolin-3-one are slowly added thereto and the mixture is boiled under reflux for 2.5 hours. The mixture is then cooled to 0°, 12 ml of 18 percent sodium hydroxide solution are added dropwise thereto and the mixture is filtered. On evaporation of the filtrate, there is obtained 8-chloro-1,1-dimethyl-1,2,3,4,5,6-hexahydrobenzo[f]quinoline as a yellow oil which is processed directly.

(c) 10.6 g (0.043 mol) of 8-chloro-1,1-dimethyl-1,2,3,4,5,6-hexahydrobenzo[f]quinoline and 6.6 ml (0.047 mol) of triethylamine are dissolved in 100 ml of methylene chloride and 3.5 ml (0.047 mol) of acetyl bromide dissolved in 20 ml of methylene chloride are added dropwise thereto at 0°. After stirring for 1 hour, the mixture is extracted with methylene chloride/water, dried with magnesium sulfate and the solvent is distilled in a vacuum. Recrystallization from methylene chloride/hexane gives 4-acetyl-8-chloro-1,1-dimethyl-1,2,3,4,5,6-hexahydrobenzo[f]quinoline as white crystals with melting point 126°-127°.

(d) 5.30 g (0.018 mol) of 4-acetyl-8-chloro-1,1-dimethyl-1,2,3,4,5,6-hexahydrobenzo[f]quinoline are dissolved in 100 ml of methylene chloride and a suspension of 8.20 g (0.04 mol) of m-chloroperbenzoic acid (85 percent) in 50 ml of methylene chloride is added dropwise thereto at 0°. After stirring at room temperature for 1.5 hours, one removes by filtration the precipitate formed and extracts with methylene chloride/water. Chromatography on silica gel with ethyl acetate/hexane (1:1) and recrystallization from ether/hexane gives 4-acetyl-11-chloro-7,7-dimethyl-1,2,4,5,6,7-hexahydro-4-benzazecine-3,8-dione as white crystals with melting point 113°-115°.

(e) 3 ml of concentrated hydrochloric acid are added to a solution of 2.40 g (0.008 mol) of 4-acetyl-11-chloro-7,7-dimethyl-1,2,4,5,6,7-hexahydro-4-benzazecine-3,8-dione in 150 ml of methanol and the mixture is stirred at room temperature for 24 hours. The solution is concentrated, extracted with methylene chloride/water, dried with magnesium sulfate and the solvent is distilled in a vacuum. Chromatography on silica gel with hexane-ethyl acetate (2:1) and then on aluminum oxide with ethyl acetate gives methyl 2-(4-acetamido-2,2-dimethyl-butyryl)-5-chloro-hydrocinnamate as a yellow oil.

EXAMPLE 17

0.3 ml of concentrated sulfuric acid is added to a solution of 10.00 g (0.032 mol) of 2-(4-acetamidobutyryl)-5-chlorohydrocinnamic acid in 40 ml of tetrahydrofuran in a steel autoclave and about 60 ml of isobutylene are condensed. The mixture is stirred at room temperature for 30 days. The solution is concentrated, extracted with methylene chloride/water, dried with magnesium sulfate and the solvent is distilled in a vacuum. Chromatography with ethyl acetate on aluminum oxide and then on silica gel gives t-butyl 2-(4-acetamidobutyryl)-5-chlorohydrocinnamate as a colorless oil.

EXAMPLE 18

2.00 g (0.006 mol) of 2-(4-acetamidobutyryl)-5-chlorohydrocinnamic acid and 0.5 ml (0.006 mol) of thionyl chloride in 20 ml of methylene chloride are stirred at room temperature for 5 minutes and then a solution of 2.2 ml (0.023 mol) of 3-hydroxymethylpyridine in 20 ml of methylene chloride is added thereto at 0°. After stirring at room temperature for 1 hour, the solution is concentrated, extracted with methylene chloride/water, dried with magnesium sulfate and the solvent is distilled in a vacuum. Chromatography on aluminum oxide with ethyl acetate gives 3-pyridylmethyl 2-(4-acetamidobutyryl)-5-chlorohydrocinnamate as a beige oil.

EXAMPLE 19

8.15 g (0.025 mol) of methyl 2-(4-acetamidobutyryl)-5-chlorohydrocinnamate are stirred at room temperature for 30 hours in 200 ml of a solution of ammonia in methanol. After concentration of the solution the residue is extracted with methylene chloride/water, dried with magnesium sulfate, the solvent is distilled in a vacuum. The residue is chromatographed on silica gel with chloroform-methanol (9:1). Recrystallization from methanol/ether yields 2-(4-acetamidobutyryl)-5-chlorohydrocinnamide as white crystals with melting point 149°-151°.

EXAMPLE 20

1.00 g (0.002 mol) of ethyl 2-[4-(4-acetamidobutyramido)butyryl]-5-chlorohydrocinnamate is stirred at room temperature for 6 days in 20 ml of a solution of ammonia in methanol. After concentration of the solution, the residue is extracted with methylene chloride/water and dried with magnesium sulfate. The solvent is distilled in a vacuum and the residue is chromatographed on aluminum oxide with ethyl acetate. Recrystallization from methanol/t-butyl methyl ether yields 2-[4-(4-acetamidobutyramido) butyryl]-5-chloro-hydrocinnamide as white crystals with melting point 126°-127°.

EXAMPLE 21

2.50 g (0.008 mol) of methyl 2-(4-acetamidobutyryl)-3-chloro-hydrocinnamate are stirred at room temperature for 2 days in 100 ml of a solution of ammonia in methanol. After concentration of the solution, the residue is extracted with methylene chloride/water, dried with magnesium sulfate and the solvent is distilled in a vacuum. Recrystallization from methanol/ether yields 2-(4-acetamidobutyryl)-3-chloro-hydrocinnamide as white crystals with melting point 148°-150°.

EXAMPLE 22

9.30 g (0.03 mol) of methyl 2-(4-acetamidobutyryl)-5-fluorohydrocinnamate are stirred at room temperature for 6 days in 200 ml of a solution of ammonia in methanol. After concentration of the solution, the residue is extracted with methylene chloride/water and dried with magnesium sulfate. The solvent is distilled in a vacuum and the residue is chromatographed on silica gel with methylene chloride-methanol (20:1). Recrystallization from methanol/ether yields 2-(4-acetamidobutyryl)-5-fluorohydrocinnamide as white crystals with melting point 125°-127°.

EXAMPLE 23

3.10 g (0.01 mol) of 2-(4-acetamidobutyryl)-5-chlorohydrocinnamic acid and 1.70 g (0.015 mol) of 1,1'-carbonyldiimidazole are stirred at room temperature for 1 hour in 30 ml of tetrahydrofuran. Then, 1.1 ml (0.015 mol) of diethylamine are added thereto at −70° and the mixture is left to warm to room temperature overnight. After concentration of the solution, the residue is extracted with methylene chloride/water, dried with magnesium sulfate and the solvent is distilled in a vacuum. Chromatography on silica gel with ethyl acetate gives 2-(4-acetamidobutyryl)-5-chloro-N,N-diethyl-hydrocinnamide as a yellow oil.

EXAMPLE 24

3.10 g (0.01 mol) of 2-(4-acetamidobutyryl)-5-chlorohydrocinnamic acid and 1.70 g (0.011 mol) of 1,1'-carbonyldiimidazole are stirred at room temperature for 1 hour in 30 ml of tetrahydrofuran. Then, 1.2 ml (0.011 mol) of 1-methylpiperazine are added thereto at −70° and the mixture is left to warm to room temperature overnight. After concentration of the solution, the residue is extracted first with methylene chloride/2N hydrochloric acid and then with methylene chloride/concentrated aqueous ammonia solution, dried with sodium sulfate and the solvent is distilled in a vacuum. Chromatography on silica gel with methylene chloride-methanol (20:1) and crystallization from ethyl acetate/hexane gives N-[3-[4-chloro-2-[2-[(4methyl-piperazin-1-yl)carbonyl]ethyl]-benzoyl]propyl]acetamide as white crystals with melting point 126°–128°.

EXAMPLE 25

3.75 g (0.012 mol) of 2-(4-acetamidobutyryl)-5-chlorohydrocinnamic acid and 2.05 g (0.013 mol) of 1,1′-carbonyldiimidazole are stirred at reflux for 1 hour in 40 ml of tetrahydrofuran and then 1.67 ml (0.013 mol) of 2-piperidinoethylamine are added thereto. After stirring at reflux temperature for 2 hours, the solution is concentrated, extracted with ethyl acetate/water (pH 14), dried with sodium sulfate and the solvent is distilled in a vacuum. Chromatography on silica gel with chloroform-methanol (4:2) and then on aluminum oxide with ethyl acetate-methanol (98:2) and subsequent crystallization from ethyl acetate/cyclohexane gives 2-(4-acetamidobutyryl)-5-chloro-N-(2-piperidinoethyl)hydrocinnamide as white crystals with melting point 103°–105°.

EXAMPLE 26

3.10 g (0.01 mol) of 2-(4-acetamidobutyryl)-5-chlorohydrocinnamic acid and 1.70 g (0.015 mol) of 1,1′-carbonyldiimidazole are stirred at room temperature for 1 hour in 30 ml of tetrahydrofuran and 1.35 g (0.015 mol) of 2-phenylethylamine are then added thereto. After stirring at room temperature for 2 hours, the solution is concentrated, extracted with methylene chloride/water, dried with magnesium sulfate and the solvent is distilled in a vacuum. Crystallization from ethyl acetate/hexane gives 2-(4-acetamidobutyryl)-5-chloro-N-phenethyl-hydrocinnamide as white crystals with melting point 127°–128°.

EXAMPLE 27

5.00 g (0.016 mol) of 2-(4-acetamidobutyryl)-5-chlorohydrocinnamic acid, 1.26 g (0.013 mol) of 4-aminopyridine and 4.16 g of N,N′-dicyclohexylcarbodiimide are stirred at room temperature for 18 hours in 100 ml of tetrahydrofuran. The solution is concentrated, extracted with ethyl acetate/water, dried with magnesium sulfate and the solvent is distilled in a vacuum. Chromatography on silica gel with ethyl acetate-methanol (4:1) and crystallization from methanol/t-butyl methyl ether gives 2-[4-acetamidobutyryl]-5-chloro-N-(4-pyridyl)hydrocinnamide as white crystals with melting point 170°–171°.

EXAMPLE 28

2.00 g (0.006 mol) of 2-(4-acetamidobutyryl)-5-chlorohydrocinnamic acid and 1.09 g (0.007 mol) of 1,1′-carbonyldiimidazole are stirred at room temperature for 1.5 hours in 20 ml of tetrahydrofuran and 1.04 g (0.007 mol) of ethyl L-alaninate hydrochloride and 0.94 ml (0.007 mol) of triethylamine are then added thereto. After stirring at room temperature for 2 hours, the mixture is extracted with methylene chloride/water, dried with magnesium sulfate and the solvent is distilled in a vacuum. Chromatography on silica gel with ethyl acetate-methanol (9:1) and then on aluminum oxide with ethyl acetate and subsequent crystallization from ethyl acetate/hexane gives ethyl N-[2-(4-acetamidobutyryl)-5-chlorohydrocinnamoyl]-L-alaninate as white crystals with melting point 106°.

EXAMPLE 29

3.10 g (0.01 mol) of 2-(4-acetamidobutyryl)-5-chlorohydrocinnamic acid and 1.70 g (0.015 mol) of 1,1′-carbonyldiimidazole are stirred at room temperature for 1 hour in 50 ml of tetrahydrofuran and 2.51 g (0.011 mol) of diethyl L-glutamate hydrochloride and 1.8 ml (0.011 mol) of N-ethyldiisopropylamine are then added thereto. After stirring at room temperature for 2 hours the solution is concentrated, extracted with methylene chloride/water, dried with sodium sulfate and the solvent is distilled in a vacuum. Chromatography on aluminum oxide with methylene chloride-methanol (97:3) and crystallization from ethyl acetate/hexane gives diethyl N-[2-(4-acetamidobutyryl)-5-chlorohydrocinnamoyl]-L-glutamate as white crystals with melting point 109°–111°.

EXAMPLE 30

1.75 g (0.006 mol) of 2-(4-acetamidobutyryl)-5-chlorohydrocinnamic acid and 0.95 g (0.006 mol) of 1,1′-carbonyldiimidazole are stirred at room temperature in 15 ml of tetrahydrofuran and 1.0 ml (0.006 mol) of N-ethyldiisopropylamine and 0.82 g (0.006 mol) of ethyl glycinate hydrochloride are then added thereto. After stirring at room temperature for 1 hour, the solution is concentrated, extracted with methylene chloride/water, dried with magnesium sulfate and the solvent is distilled in a vacuum. Chromatography on aluminum oxide with ethyl acetate-ethanol (9:1) and crystallization from methylene chloride/t-butyl methyl ether gives ethyl N-[2-(4-acetamidobutyryl)-5-chlorohydrocinnamoyl]-glycinate as white crystals with melting point 96°.

EXAMPLE 31

3.00 g (0.008 mol) of ethyl N-[2-(4-acetamidobutyryl)-5-chlorohydrocinnamoyl]glycinate are stirred at room temperature for 3 days in 30 ml of a solution of ammonia in methanol. After concentration of the solution, the residue is extracted with methylene chloride/water, dried with magnesium sulfate and the solvent is distilled in a vacuum. Recrystallization from methanol/t-butyl methyl ether yields 2-(4-acetamidobutyryl)-N-(carbamoylmethyl)-5-chlorohydrocinnamide as white crystals with melting point 148°–149°.

EXAMPLE 32

0.38 g (0.01 mol) of sodium borohydride is added to a solution of 3.25 g (0.01 mol) of methyl 2-(4-acetamidobutyryl)-5-chloro-hydrocinnamate in 35 ml of methanol and the mixture is stirred at room temperature for 1 hour. The solution is concentrated, extracted with methylene chloride/water, dried with magnesium sulfate and the solvent is distilled in a vacuum. Chromatography on silica gel with chloroform-methanol (20:1) gives methyl 2-(4-acetamido-1-hydroxybutyl)-5-chlorohydrocinnamate as a yellow oil.

EXAMPLE 33

A suspension of 15.5 g (0.05 mol) of 2-(4-acetamidobutyryl)-5-chlorohydrocinnamic acid and 8.50 g (0.052 mol) of 1,1′-carbonyldiimidazole in 350 ml of tetrahydrofuran is stirred at room temperature for 2 hours and 4.00 g (0.052 mol) of glycolamide are added thereto. After stirring at room temperature overnight, the solution is concentrated, extracted with methylene chloride/water, dried with magnesium sulfate and the solvent is distilled in a vacuum. Chromatography on silica gel with methylene chloride-methanol (20:1) and crystallization from ethyl acetate/ether gives carbamoylmethyl 2-(4-acetamidobutyryl)-5-chlorohydrocinnamate as white crystals with melting point 114°–116°.

EXAMPLE 34

3.10 g (0.01 mol) of 2-(4-acetamidobutyryl)-5-chlorohydrocinnamic acid and 1.70 g (0.01 mol) of 1,1'-carbonyldiimidazole are suspended in 30 ml of tetrahydrofuran, stirred at room temperature for 1 hour and treated with 2.50 g (0.01 mol) of N-(2-aminoethyl)-5-chloro-2-pyridinecarboxamide hydrochloride and 1.8 ml (0.01 mol) of ethyldiisopropylamine. After 2 hours the mixture is concentrated, extracted with ethyl acetate/water and recrystallized from methanol/ether. The 2-(4-acetamidobutyryl)-5-chloro-N-[2-(5-chloro-2-pyridinecarboxamido)ethyl]hydrocinnamide obtained melts at 163°–165°.

EXAMPLE 35

(a) 8.00 g (0.06 mol) of aluminum chloride are suspended in 600 ml of methylene chloride, treated at 0° with 7.56 g (0.04 mol) of 4-chlorophenylacetyl chloride in 250 ml of methylene chloride and a solution of 4.17 g (0.04 mol) of styrene in 400 ml of methylene chloride is added dropwise thereto at −40° to −50°. After warming to room temperature, the mixture is poured on to ice, extracted with methylene chloride, dried with magnesium sulfate, filtered over Dicalit and the solvent is distilled in a vacuum. Chromatography on silica gel with ethyl acetate-hexane (1:4) and recrystallization from ether/hexane gives 6-chloro-3,4-dihydro-4-phenyl-2(1H)-naphthalenone as beige crystals with melting point 61°–62°.

(b) A solution of 73.3 g (0.23 mol) of 6-chloro-3,4-dihydro-4-phenyl-2(1H)-naphthalenone in 1.5 l of toluene is treated with 32.4 g (0.58 mol) of potassium hydroxide and 83.7 g (0.64 mol) of 3-chloropropylamine hydrochloride and boiled on a water separator for 42 hours. After cooling to room temperature, there are added thereto 79 ml (0.56 mol) of triethylamine and dropwise 29.7 ml (0.42 mol) of acetyl chloride in 250 ml of toluene. The mixture is stirred for 1 hour, extracted with ethyl acetate/water, dried with magnesium sulfate and the solvent is distilled in a vacuum. Chromatography over silica gel with hexane-ethyl acetate (4:1) and then with hexane-ethyl acetate (1:1) and recrystallization from ethyl acetate gives 4-acetyl-8-chloro-1,2,3,4,5,6-hexahydro-6-phenylbenzo[f]quinoline as beige crystals with melting point 167°–168°.

(c) 8.13 g (0.04 mol) of m-chloroperbenzoic acid (85 percent) in 80 ml of methylene chloride are added to a solution of 6.60 g (0.02 mol) of 4-acetyl-8-chloro-1,2,3,4,5,6-hexahydro-6-phenylbenzo[f]quinoline in 70 ml of methylene chloride and the mixture is stirred at room temperature for 1 hour. The mixture is filtered, extracted with methylene chloride/saturated sodium hydrogen carbonate solution, dried with magnesium sulfate and the solvent is distilled in a vacuum. Crystallization from methylene chloride/hexane gives 4-acetyl-11-chloro-1-phenyl-1,2,4,5,6,7-hexahydro-4-benzazecine-3,8-dione as white crystals with melting point 184°–185°.

(d) A solution of 3.30 g (0.009 mol) of 4-acetyl-11-chloro-1-phenyl-1,2,4,5,6,7-hexahydro-4-benzazecine-3,8-dione in 40 ml of tetrahydrofuran and 20 ml of 2N hydrochloric acid is stirred at room temperature for two days. Then, the solution is concentrated, extracted with methylene chloride/water, dried with magnesium sulfate and the solvent is distilled in a vacuum. Chromatography on silica gel with hexane-ethyl acetate (1:1) and crystallization from ethyl acetate/hexane gives 2-(4-acetamidobutyryl)-5-chloro-β-phenylhydrocinnamic acid as white crystals with melting point 114°–116°.

EXAMPLE 36

5.2 ml (0.005 mol) of 1N sodium hydroxide solution are added to a suspension of 2.00 g (0.005 mol) of 2-(4-acetamidobutyryl)-5-chloro-β-phenylhydrocinnamic acid in 120 ml of water. The mixture is treated slowly with 0.88 g (0.005 mol) of silver nitrate in 1 ml of water and stirred at room temperature overnight. The precipitate formed is removed by filtration and stirred overnight with 50 ml of ethyl iodide. The mixture is extracted with methylene chloride/water, dried with magnesium sulfate and the solvent is distilled in a vacuum. Chromatography on silica gel with hexane-ethyl acetate (1:1) and on aluminum oxide with hexane-ethyl acetate (1:1) gives ethyl 2-(4-acetamidobutyryl)-5-chloro-β-phenylhydrocinnamate as a colorless oil.

EXAMPLE 37

120 ml of 2N hydrochloric acid are added to a solution of 23.8 g (0.06 ml) of N-[3-[(11-chloro-2,3,5,6,7,8-hexahydro-3,8-dioxo-4-benzazecin-4(1H)-yl)-carbonyl]-propyl]acetamide in 240 ml of tetrahydrofuran and the mixture is stirred at room temperature for 8 days. The solution is concentrated, extracted with methylene chloride/water, dried with magnesium sulfate and the solvent is distilled in a vacuum. Recrystallization from methanol/ether gives 2-[4-(4-acetamidobutyramido)-butyryl]-5-chlorohydrocinnamic acid as beige crystals with melting point 108°.

EXAMPLE 38

6.00 g (0.015 mol) of 2-[4-(4-acetamidobutyramido)-butyryl]-5-chlorohydrocinnamic acid and 2.57 g (0.016 mol) of 1,1'-carbonyldiimidazole are stirred at room temperature for 1.5 hours in 60 ml of tetrahydrofuran and 2.22 g (0.016 mol) of ethyl glycinate hydrochloride and 2.2 ml (0.016 mol) of triethylamine are added thereto. After stirring at room temperature for 1 hour, the solution is concentrated, extracted with methylene chloride/water, dried with magnesium sulfate and the solvent is distilled in a vacuum. Chromatography on silica gel with ethyl acetate-ethanol (9:1) and crystallization from methanol-ether gives ethyl N-[2-[4-(4-acetamidobutyramido)butyryl]-5-chlorohydrocinnamoyl]glycinate as white crystals with melting point 94°–96°.

EXAMPLE 39

2.50 g (0.005 mol) of ethyl N-[2-[4-(4-acetamidobutyramido)butyryl]-5-chlorohydrocinnamoyl]glycinate are stirred at room temperature overnight in 50 ml of a solution of ammonia in methanol. After concentration of the solution the residue is extracted with methylene chloride/water, dried with magnesium sulfate and the solvent is distilled in a vacuum. Two-fold recrystallization from methanol/ether gives 2-[4-(4-acetamidobutyramido)butyryl]-N-(carbamoylmethyl)-5-chlorohydrocinnamide as white crystals with melting point 172°-174°.

EXAMPLE 40

15 ml of 2N sodium hydroxide solution are added to a solution of 1.50 g (0.004 mol) of ethyl N-[2-(4-acetamidobutyryl)-5-chlorohydrocinnamoyl]glycinate in 15 ml of tetrahydrofuran and the mixture is stirred at room temperature for 1 hour. After acidification with 17 ml of 2N hydrochloric acid, the mixture is extracted with ethyl acetate/water, dried with magnesium sulfate and the solvent is distilled in a vacuum. Recrystallization from ethyl acetate/ether yields N-[2-(4-acetamidobutyryl)-5-chlorohydrocinnamoyl]glycine as white crystals with melting point 88°-89°.

EXAMPLE 41

(a) 25.0 g (0.115 mol) of 8-chloro-1,2,3,4,5,6-hexhydrobenzo[f]quinoline are dissolved in 145 ml of methylene chloride. Then, 21.8 g (0.182 mol) of α-chloroacetyl isocyanate in 30 ml of methylene chloride are added dropwise thereto at 0° and the mixture is stirred at room temperature overnight. After the addition of 200 ml of methanol, the mixture is again stirred for 24 hours and the resulting 8-chloro-N-(chloroacetyl)-2,3,5,6-tetrahydrobenzo[f]quinoline-4(1H)-carboxamide which exhibits a melting point of 158°-161° after recrystallization from ethyl acetate/ether, is removed by filtration. An additional amount of the above product can be obtained from the filtrate and the mother liquor.

(b) A suspension of 11.85 g (0.035 mol) of 8-chloro-N-(chloroacetyl)-2,3,5,6-tetrahydrobenzo[f]quinoline-4(1H)-carboxamide and 4.4 ml (0.091 mol) of hydrazine hydrate in 250 ml of ethanol is stirred at room temperature for 3 hours, concentrated in a vacuum and extracted with methylene chloride/water. Drying with magnesium sulfate and distillation of the solvent in a vacuum yields 8-chloro-2,3,5,6-tetrahydrobenzo[f]quinoline-4(1H)-carboxamide as white crystals which exhibit a melting point of 169°-171° after recrystallization from methylene chloride.

(c) 9.20 g (0.035 mol) of 8-chloro-2,3,5,6-tetrahydrobenzo[f]quinoline-4(1H)-carboxamide are suspended in 100 ml of methylene chloride and 14.1 g (0.071 mol) of m-chloroperbenzoic acid (85 percent) in 150 ml of methylene chloride are added dropwise thereto at 10°-15°. After stirring at room temperature for 1.5 hours, the mixture is poured into saturated sodium hydrogen carbonate solution, extracted with methylene chloride, dried with magnesium sulfate and the solvent is distilled in a vacuum. The solid obtained is washed with hot ethyl acetate. Recrystallization from dioxane/ether yields 11-chloro-2,3,5,6,7,8-hexahydro-3,8-dioxo-4-benzazecine-4(1H)-carboxamide as white crystals with melting point 182°-184°.

(d) 7 ml of concentrated hydrochloric acid are added to a solution of 6.80 g (0.023 mol) of 11-chloro-2,3,5,6,7,8-hexahydro-3,8-dioxo-4-benzazecine-4(1H)-carboxamide in 5 l of ethanol and the mixture is stirred at room temperature for 13 days. The solution is concentrated, extracted with methylene chloride/water, dried with magnesium sulfate and the solvent is distilled in a vacuum. Chromatography on silica gel with methylene chloride/methanol (97:3) and crystallization from ethyl acetate/hexane gives ethyl 5-chloro-2-(4-ureidobutyryl)hydrocinnamate as white crystals with melting point 127°-129°.

EXAMPLE A

Tablets of the following composition, which contain ethyl N-[2-(4-acetamidobutyryl)-5-chlorohydrocinnamoyl]glycinate as the active substance, are prepared.

|   | Per tablet |
| --- | --- |
| 1. Active substance (micronized) | 50 mg |
| 2. Lactose | 120 mg |
| 3. Maize starch | 50 mg |
| 4. Polyvinylpyrrolidone | 8 mg |
| 5. Sodium carboxymethylstarch | 20 mg |
| 6. Magnesium stearate | 2 mg |
|  | 250 mg |

The active substance is mixed homogeneously with a mixture of lactose and maize starch. The mixture is sieved, moistened with an aqueous polyvinylpyrrolidone solution, granulated and dried. The dried granulate is mixed with sodium carboxymethylstarch and magnesium stearate and the thus-obtained mixture is pressed to tablets of suitable size with a break-bar.

EXAMPLE B

Tablets of the following composition, which contain ethyl N-[2-(4-acetamidobutyryl)-5-chlorohydrocinnamoyl]glycinate as the active substance, are prepared.

|   | Per tablet |
| --- | --- |
| 1. Active substance (micronized) | 10 mg |
| 2. Lactose | 88 mg |
| 3. Microcrystalline cellulose | 60 mg |
| 4. Maize starch | 20 mg |
| 5. Sodium carboxymethylstarch | 20 mg |
| 6. Magnesium stearate | 2 mg |
|  | 200 mg |

The active substance is mixed homogeneously with lactose. The mixture is sieved. Then a mixture of microcrystalline cellulose, maize starch and sodium carboxymethylstarch is admixed therewith and the resulting mixture is blended with the magnesium stearate. The thus-obtained ready-to-press mixture is processed to tablets of suitable size with a break-bar.

EXAMPLE C

Tablets of the following composition, which contain ethyl N-[2-(4-acetamidobutyryl)-5-chlorohydrocinnamoyl]glycinate as the active substance, are prepared.

|   | Per tablet |
| --- | --- |
| 1. Active substance (micronized) | 0.10 mg |
| 2. Lactose | 126.90 mg |
| 3. Maize starch | 50.00 mg |
| 4. Polyvinylpyrrolidone | 6.00 mg |
| 5. Sodium carboxymethylstarch | 15.00 mg |
| 6. Magnesium stearate | 2.00 mg |
|  | 200.00 mg |

The active substance is mixed homogeneously with a mixture of lactose and maize starch. The mixture is sieved, moistened with an aqueous polyvinylpyrrolidone solution, granulated and dried. The dried granulate is mixed with sodium carboxymethylstarch and magnesium stearate and the thus-obtained mixture is pressed to tablets of suitable size with a break-bar.

We claim:

1. A compound of the formula

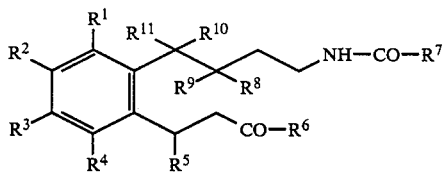

wherein
one or two or the symbols $R^1$ to $R^4$ are halogen or methoxy and the others are hydrogen;
$R^5$ is hydrogen or phenyl;
$R^6$ is a residue of the formula $$-OR^{12} \quad \text{or} \quad -NR^{13}R^{14};$$
(a) (b)

$R^7$ is $(C_1-C_4)$-alkyl, $(C_2-C_5)$-alkanoylamino-$(C_2-C_5)$-alkyl, amino or $(C_1-C_4)$-alkoxyphenyl;
$R^8$ and $R^9$ each, independently, are hydrogen or $(C_1-C_4)$-alkyl;
$R^{10}$ is hydrogen and $R_{11}$ is hydroxy or $R^{10}$ and $R^{11}$ taken together are oxo;
$R^{12}$ is hydrogen, $(C_1-C_{10})$-alkyl, pyridylmethyl or carbamoylmethyl;
$R^{13}$ is hydrogen, $(C_1-C_4)$-alkyl and $R^{14}$ is hydrogen, $(C_1-C_4)$-alkyl, pyridyl, phenyl-$(C_1-C_4)$-alkyl, carboxy-$(C_1-C_4)$-alkyl, carbamoyl-$(C_1-C_4)$-alkyl, $(C_1-C_{alkoxycarbonyl}-(C_1-C_4)$-alkyl, di-$(C_1-C_4)$-alkoxycarbonyl-$(C_2-C_5C_5)$-alkyl, piperidino-$(C_2-C_4)$-alkyl or halopyridinecarboxamido-$(C_2-C_4)$-alkyl or $R^{13}$ and $R^{14}$ taken together with the nitrogen atom are 4-$(C_1-C_4)$-alkyl-piperazin-1-yl,
or a pharmaceutically acceptable salt of a basic compound of formula I with an acid or of an acidic compound of formula I with a base.

2. A compound in accordance with claim 1, wherein $R^4$ is hydrogen and either $R^1$ is chlorine and $R^2$ and $R^3$ are hydrogen or $R^1$ is hydrogen and $R^2$ and $R^3$ are chlorine or $R^1$ and $R^2$ are hydrogen and $R^3$ is fluorine, chlorine or methoxy.

3. A compound in accordance with claim 2, wherein $R^3$ is chlorine and $R^1$, $R^2$ and $R^4$ are hydrogen.

4. A compound in accordance with claim 2, wherein $R^5$ is hydrogen.

5. A compound in accordance with claim 2, wherein $R^6$ is a residue of formula (a) or (b) in which $R^{12}$ is hydrogen, methyl, ethyl, n-propyl, isopropyl, n-butyl, tert.-butyl, n-nonyl, 5-nonyl, 3-pyridylmethyl or carbamoylmethyl or either $R^{13}$ and $R^{14}$ both are hydrogen or both are ethyl or $R^{13}$ and $R^{14}$ taken together with the nitrogen atom are 4-methylpiperazin-1-yl or $R^{13}$ is hydrogen and $R^{14}$ is 4-pyridyl, 2-phenylethyl, 2-piperidinoethyl, carboxymethyl, ethoxycarbonylmethyl, carbamoylmethyl, 1-ethoxycarbonylethyl, 1,4-bis-(ethoxycarbonyl)-2-butyl or 2-(5-chloro-2-pyridinecarboxamido)ethyl.

6. A compound in accordance with claim 5, wherein $R^{12}$ is ethyl, n-propyl, isopropyl, n-nonyl or carbamoylmethyl or $R^{13}$ is hydrogen and $R^{14}$ is hydrogen, ethoxycarbonylmethyl or 1,4-bis-(ethoxycarbonyl)-2-butyl.

7. A compound in accordance with claim 2, wherein $R^7$ is methyl, 3-acetylaminopropyl, amino or p-methoxyphenyl.

8. A compound in accordance with claim 7, wherein $R^7$ is methyl or 3-acetylaminopropyl.

9. A compound in accordance with claim 2, wherein $R^8$ and $R^9$ both are hydrogen or both are methyl.

10. A compound in accordance with claim 9, wherein $R^8$ and $R^9$ both are hydrogen.

11. A compound in accordance with claim 2, wherein $R^{10}$ and $R^{11}$ together are oxo.

12. A compound in accordance with claim 1, ethyl N-[2-(4-acetamidobutyryl)-5-chlorohydrocinnamoyl]-glycinate.

13. A compound in accordance with claim 1, ethyl 2-[4-(4-acetamidobutyramido)butyryl]-5-chlorohydrocinnamate.

14. A compound in accordance with claim 1, 2-[4-(4-acetamidobutyramido)butyryl]-5-chlorohydrocinnamide.

15. A compound in accordance with claim 1, isopropyl 2-(4-acetamidobutyryl)-5-chlorohydrocinnamate.

16. A compound in accordance with claim 1, ethyl 2-(4-acetamidobutyryl)-5-chlorohydrocinnamate.

17. A compound in accordance with claim 1, diethyl 2-[2-(4-acetamidobutyryl)-5-chlorohydrocinnamoyl]-L-glutamate.

18. A compound in accordance with claim 1, carbamoylmethyl 2-(4-acetamidobutyryl)-5-chlorohydrocinnamate.

19. A compound in accordance with claim 1, 2-(4-Acetamidobutyryl)-5-chlorohydrocinnamide.

20. A compound in accordance with claim 1, propyl 2-(4-acetamidobutyryl)-5-chlorohydrocinnamate.

21. A compound in accordance with claim 1, 2-(4-acetamidobutyryl)-N-(carbamoylmethyl)-5-chlorohydrocinnamide.

22. A compound in accordance with claim 1, nonyl 2-(4-acetamidobutyryl)-5-chlorohydrocinnamate.

23. A pharmaceutical composition comprising a therapeutically effective amount of a compound of the formula

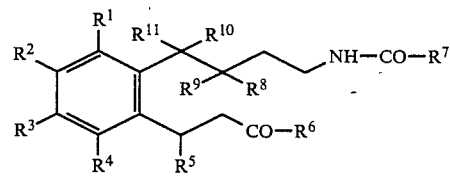

wherein
one or two of the symbols $R^1$ to $R^4$ are halogen or methoxy and the others are hydrogen;
$R^5$ is hydrogen or phenyl;
$R^6$ is a residue of the formula $$-OR^{12} \quad \text{or} \quad -NR^{13}R^{14};$$
(a) (b)

$R^7$ is $(C_1-C_4)$-alkyl, $(C_2-C_5)$-alkanoylamino-$(C_2-C_5)$-alkyl, amino or $(C_1-C_4)$-alkoxyphenyl;
$R^8$ and $R^9$ each, independently, are hydrogen or $(C_1-C_4)$-alkyl;
$R^{10}$ is hydrogen and $R^{11}$ is hydroxy or $R^{10}$ and $R^{11}$ taken together are oxo;

$R^{12}$ is hydrogen, $(C_1-C_{10})$-alkyl, pyridylmethyl or carbamoylmethyl;

$R^{13}$ is hydrogen, $(C_1-C_4)$-alkyl and $R^{14}$ is hydrogen, $(C_1-C_4)$-alkyl, pyridyl, phenyl-$(C_1-C_4)$-alkyl, carboxy-$(C_1-C_4)$-alkyl, carbamoyl-$(C_1-C_4)$-alkyl, $(C_1-C_4)$-alkoxycarbonyl-$(C_1-C_4)$-alkyl, di-$(C_1-C_4)$-alkoxycarbonyl-$(C_2-C_5)$-alkyl, piperidino-$(C_2-C_4)$-alkyl or halopyridinecarboxamido-$(C_2-C_4)$-alkyl or $R^{13}$ and $R^{14}$ taken together with the nitrogen atom are 4-$(C_1-C_4)$-alkyl-piperazin-1-yl, or a pharmaceutically acceptable salt of a basic compound of formula I with an acid or of an acidic compound of formula I with a base.

24. A pharmaceutical composition in accordance with claim 23, wherein $R^4$ is hydrogen and either $R^1$ is chlorine and $R^2$ and $R^3$ are hydrogen or $R^1$ is hydrogen and $R^2$ and $R^3$ are chlorine or $R^1$ and $R^2$ are hydrogen and $R^3$ is fluorine, chlorine or methoxy.

25. A pharmaceutical composition in accordance with claim 24, wherein $R^3$ is chlorine and $R^1$, $R^2$ and $R^4$ are hydrogen.

26. A pharmaceutical composition in accordance with claim 24, wherein $R^5$ is hydrogen.

27. A pharmaceutical composition in accordance with claim 24, wherein $R^6$ is a residue of formula (a) or (b) in which $R^{12}$ is hydrogen, methyl, ethyl, n-propyl, isopropyl, n-butyl, tert.-butyl, n-nonyl, 5-nonyl, 3-pyridylmethyl or carbamoylmethyl or either $R^{13}$ and $R^{14}$ both are hydrogen or both are ethyl or $R^{13}$ and $R^{14}$ taken together with the nitrogen atom are 4-methylpiperazin-1-yl or $R^{13}$ is hydrogen and $R^{14}$ is 4-pyridyl, 2-phenylethyl, 2-piperidinoethyl, carboxymethyl, ethoxycarbonylmethyl, carbamoylmethyl, 1-ethoxycarbonylethyl, 1,4-bis-(ethoxycarbonyl)-2-butyl or 2-(5-chloro-2-pyridinecarboxamido)ethyl.

28. A pharmaceutical composition in accordance with claim 24, wherein $R^7$ is methyl, 3-acetylaminopropyl, amino or p-methoxyphenyl.

29. A pharmaceutical composition in accordance with claim 24, wherein $R^8$ and $R^9$ both are hydrogen or both are methyl.

30. A pharmaceutical composition in accordance with claim 23, wherein the compound of formula I is ethyl N-[2-(4-acetamidobutyryl)-5-chlorohydrocinnamoyl]glycinate.

31. A pharmaceutical composition in accordance with claim 23, wherein the compound of the formula I is ethyl 2-[4-(4-acetamidobutyramido)butyryl]-5-chlorohydrocinnamate.

32. A pharmaceutical composition in accordance with claim 23, wherein the compound of formula I is 2-[4-(4-acetamidobutyramido)butyryl]-5-chlorohydrocinnamide.

* * * * *

UNITED STATES PATENT AND TRADEMARK OFFICE
CERTIFICATE OF CORRECTION

PATENT NO. : 4,883,815

DATED : November 28, 1989

INVENTOR(S) : Aschwanden et al

It is certified that error appears in the above-identified patent and that said Letters Patent is hereby corrected as shown below:

ON TITLE PAGE: item 75 Inventors:
name should read "Aschwanden".

In column 31, line 35, claim 1, please delete
"$(C_1-C-\text{alkoxycarbonyl}-$" and insert -- $(C_1-C_4)-\text{alkoxycarbonyl}$ --;

Column 31, claim 1, line 36, please delete "$(C_2-C_5C_5)$" and insert
-- $(C_2-C_5)$ --

Signed and Sealed this

Nineteenth Day of November, 1991

Attest:

HARRY F. MANBECK, JR.

*Attesting Officer*  *Commissioner of Patents and Trademarks*